US010925649B2

(12) United States Patent
Semingson et al.

(10) Patent No.: US 10,925,649 B2
(45) Date of Patent: Feb. 23, 2021

(54) ARTICULATING ROD INSERTER

(71) Applicant: Spinal Elements, Inc., Carlsbad, CA (US)

(72) Inventors: Taylor Semingson, San Diego, CA (US); Jason Blain, Encinitas, CA (US)

(*) Notice: Subject to any disclaimer, the term of this patent is extended or adjusted under 35 U.S.C. 154(b) by 53 days.

(21) Appl. No.: 15/694,668

(22) Filed: Sep. 1, 2017

(65) Prior Publication Data
US 2017/0360486 A1 Dec. 21, 2017

Related U.S. Application Data

(62) Division of application No. 14/822,780, filed on Aug. 10, 2015, now Pat. No. 9,750,546.

(60) Provisional application No. 62/036,053, filed on Aug. 11, 2014.

(51) Int. Cl.
*A61B 17/70* (2006.01)
*A61B 17/56* (2006.01)

(52) U.S. Cl.
CPC ........ *A61B 17/7085* (2013.01); *A61B 17/708* (2013.01); *A61B 17/7082* (2013.01); *A61B 17/7083* (2013.01); *A61B 2017/564* (2013.01)

(58) Field of Classification Search
USPC ................................. 606/914, 86 A
See application file for complete search history.

(56) References Cited

U.S. PATENT DOCUMENTS

| | | | |
|---|---|---|---|
| 6,183,472 B1* | 2/2001 | Lutz | A61B 17/7032 606/104 |
| 6,342,057 B1 | 1/2002 | Brace et al. | |
| 6,530,929 B1 | 3/2003 | Justis et al. | |
| 6,660,022 B1 | 12/2003 | Li et al. | |
| 6,736,829 B1 | 5/2004 | Li et al. | |
| 6,830,574 B2 | 12/2004 | Heckele et al. | |
| 6,916,323 B2 | 7/2005 | Kitchens | |
| 7,008,422 B2 | 3/2006 | Foley et al. | |
| 7,011,660 B2 | 3/2006 | Sherman et al. | |
| 7,041,120 B2 | 5/2006 | Li et al. | |

(Continued)

FOREIGN PATENT DOCUMENTS

| | | |
|---|---|---|
| EP | 2098178 B1 | 12/2011 |
| EP | 1558157 B1 | 11/2012 |

(Continued)

OTHER PUBLICATIONS

McAfee PC, Regan JJ, Geis WP, Fedder IL. Minimally Invasive Anterior Retroperitoneal Approach to the Lumbar Spine. *Spine* 1998; 23(13): p. 1476-1484.

(Continued)

*Primary Examiner* — Jan Christopher L Merene

(57) ABSTRACT

An articulating rod inserter is configured for use in delivering a fixation rod to an orthopedic fixation system through a cannula or tower. The articulating rod inserter is releasably coupled to a rod and can move the rod from a generally aligned configuration, wherein the longitudinal axes of the rod and rod inserter are generally aligned, to an angled configuration, wherein the longitudinal axis of the rod is at an angle to the longitudinal axis of the rod inserter. The rod is inserted into the patient through a first tower and then articulated to a second tower such that the rod extends between two or more fixation devices.

12 Claims, 25 Drawing Sheets

(56) References Cited

U.S. PATENT DOCUMENTS

| | | |
|---|---|---|
| 7,083,612 B2 | 8/2006 | Littrup et al. |
| 7,188,626 B2 | 3/2007 | Foley et al. |
| 7,250,052 B2 | 7/2007 | Landry et al. |
| 7,306,603 B2 | 12/2007 | Boehm, Jr. et al. |
| 7,322,979 B2 | 1/2008 | Crandall et al. |
| 7,431,731 B2 | 10/2008 | Kitchens |
| 7,473,267 B2 | 1/2009 | Nguyen et al. |
| 7,476,240 B2 | 1/2009 | Raymond et al. |
| 7,491,218 B2 | 2/2009 | Landry et al. |
| 7,497,869 B2 | 3/2009 | Justis |
| 7,520,879 B2 | 4/2009 | Justis et al. |
| 7,527,638 B2 | 5/2009 | Anderson et al. |
| 7,563,264 B2 | 7/2009 | Landry et al. |
| 7,572,276 B2 | 8/2009 | Lim et al. |
| 7,588,575 B2 | 9/2009 | Colleran et al. |
| 7,588,588 B2 | 9/2009 | Spitler et al. |
| 7,597,694 B2 | 10/2009 | Lim et al. |
| 7,618,442 B2 | 11/2009 | Spitler et al. |
| 7,648,506 B2 | 1/2010 | McCord et al. |
| 7,648,507 B2 | 1/2010 | Techiera et al. |
| 7,666,189 B2 | 2/2010 | Gerber et al. |
| 7,686,809 B2 | 3/2010 | Triplett et al. |
| 7,691,132 B2 | 4/2010 | Landry et al. |
| 7,695,475 B2 | 4/2010 | Justis et al. |
| 7,717,944 B2 | 5/2010 | Foley et al. |
| 7,749,232 B2 | 7/2010 | Salerni |
| 7,758,617 B2 | 7/2010 | Iott et al. |
| 7,763,030 B2 | 7/2010 | Blau et al. |
| 7,763,055 B2 | 7/2010 | Foley |
| 7,794,479 B2 | 9/2010 | Aferzon |
| 7,824,410 B2 | 11/2010 | Simonson et al. |
| 7,862,595 B2 | 1/2011 | Foley et al. |
| 7,871,413 B2 | 1/2011 | Park et al. |
| 7,871,424 B2 | 1/2011 | Abdelgany |
| 7,875,031 B2 | 1/2011 | Chin et al. |
| 7,905,907 B2 | 3/2011 | Spitler et al. |
| 7,909,830 B2 | 3/2011 | Frigg et al. |
| 7,914,558 B2 | 3/2011 | Landry et al. |
| 7,918,878 B2 | 4/2011 | Songer et al. |
| 7,922,727 B2 | 4/2011 | Songer et al. |
| 7,922,731 B2 | 4/2011 | Schumacher et al. |
| 7,951,152 B2 | 5/2011 | Marino |
| 7,967,826 B2 | 6/2011 | Colleran et al. |
| 7,976,546 B2 | 7/2011 | Geist et al. |
| 7,998,144 B2 | 8/2011 | Schumacher et al. |
| 8,002,798 B2 | 8/2011 | Chin et al. |
| 8,034,084 B2 | 10/2011 | Landry et al. |
| 8,048,129 B2 | 11/2011 | Forton et al. |
| 8,070,751 B2 | 12/2011 | Justis et al. |
| 8,075,592 B2 | 12/2011 | Landry et al. |
| 8,097,027 B2 | 1/2012 | Lim et al. |
| 8,100,951 B2 | 1/2012 | Justis et al. |
| 8,105,362 B2 | 1/2012 | Duarte |
| 8,162,952 B2 | 4/2012 | Cohen et al. |
| 8,182,509 B2 | 5/2012 | Abdelgany |
| 8,192,439 B2 | 6/2012 | Songer et al. |
| 8,211,153 B2 | 7/2012 | Shaolian et al. |
| 8,246,624 B2 | 8/2012 | Forton et al. |
| 8,308,728 B2 | 11/2012 | Iott et al. |
| 8,317,838 B2 | 11/2012 | Nguyen et al. |
| 8,323,286 B2 | 12/2012 | Justis |
| 8,343,160 B2 | 1/2013 | Techiera et al. |
| 8,366,714 B2 | 2/2013 | Jones et al. |
| 8,366,715 B2 | 2/2013 | Geist et al. |
| 8,414,588 B2 | 4/2013 | Stad et al. |
| 8,414,590 B2 | 4/2013 | Oh et al. |
| 8,425,531 B2 | 4/2013 | Salerni |
| 8,435,245 B2 | 5/2013 | Oh |
| 8,460,300 B2 | 6/2013 | Hestad et al. |
| 8,460,301 B2 | 6/2013 | Fiorella |
| 8,469,960 B2 | 6/2013 | Hutton et al. |
| 8,540,719 B2 | 9/2013 | Peukert et al. |
| 8,734,490 B2 | 5/2014 | Anderson et al. |
| 9,161,786 B2 | 10/2015 | Anderson et al. |
| 2005/0131408 A1* | 6/2005 | Sicvol ............... A61B 17/7032 606/86 A |
| 2006/0069391 A1* | 3/2006 | Jackson ............. A61B 17/7038 606/62 |
| 2007/0173831 A1 | 7/2007 | Abdou |
| 2008/0077138 A1 | 3/2008 | Cohen et al. |
| 2011/0022088 A1 | 1/2011 | Forton et al. |
| 2011/0218581 A1* | 9/2011 | Justis ................... A61B 17/708 606/86 A |
| 2012/0031792 A1* | 2/2012 | Petit ...................... A61B 50/30 206/438 |
| 2012/0265305 A1 | 10/2012 | Oh et al. |
| 2014/0100613 A1 | 4/2014 | Iott et al. |
| 2015/0051653 A1 | 2/2015 | Cryder et al. |
| 2016/0038196 A1* | 2/2016 | Smith ............... A61B 17/7083 606/86 A |

FOREIGN PATENT DOCUMENTS

| | | |
|---|---|---|
| JP | 2012521812 | 9/2012 |
| JP | 2013521062 | 6/2013 |
| KR | 1001539 | 12/2010 |
| KR | 20140035296 | 3/2014 |

OTHER PUBLICATIONS

Foley KT, Gupta SK. Percutaneous Pedicle Screw Fixation of the Lumbar Spine: Preliminary Clinical Results. *Journal of Neurosurgery* 2002; 97(S1): p. 7-12.

Kim DH, Jaikumar S, Kam AC. Minimally Invasive Spine Instrumentation. *Neurosurgery* 2002; 51(S2): p. 15-25.

Khoo LT, Palmer S, Laich DT, Fessler RG. Minimally Invasive Percutaneous Posterior Lumbar Interbody Fusion. *Neurosurgery* 2002; 51(S2): p. 166-181.

Wang MY, Prusmack CJ, Green BA, Gruen JP, Levi AD. Minimally Invasive Lateral Mass Screws in the Treatment of Cervical Facet Dislocations: Technical Note. *Neurosurgery* 2003; 52(2): p. 444-448.

Shamie AN, Mroz T, Suen P, Wang JC. Minimally Invasive Spinal Surgery. *Operative Techniques in Orthopaedics* 2003; 13(3): p. 202-206.

Newton PO, Lee SS, Mahar AT, Farnsworth CL, Weinstein CH. Thoracoscopic Multilevel Anterior Instrumented Fusion in a Goat Model. *Spine* 2003; 28(14): p. 1614-1620.

Foley KT, Holly LT, Schwender JD. Minimally Invasive Lumbar Fusion. *Spine* 2003; 28(S15): p. S26-S35.

International Search Report and Written Opinion for International Application No. PCT/US2015/044527, dated Feb. 4, 2016.

Extended European Search Report dated Mar. 8, 2018.

\* cited by examiner

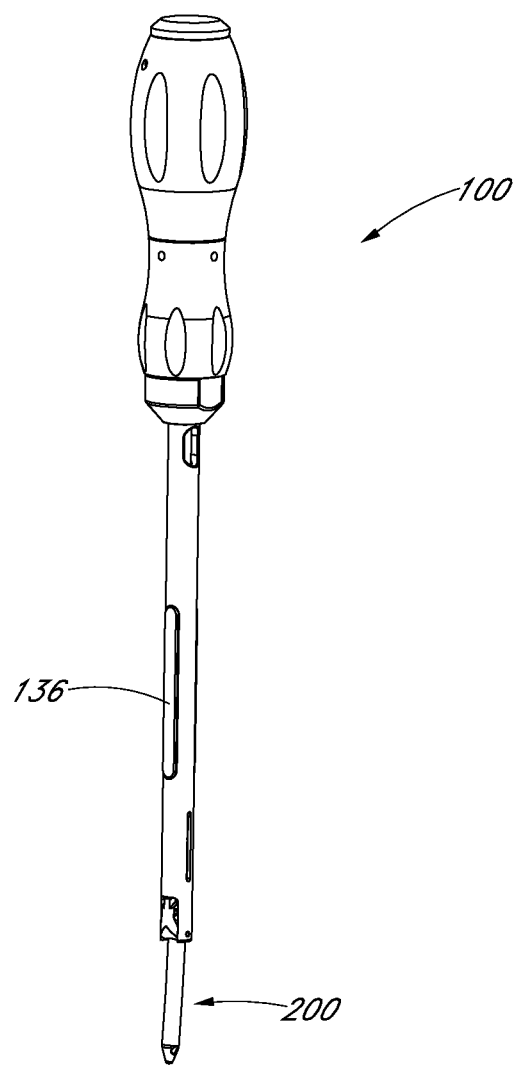
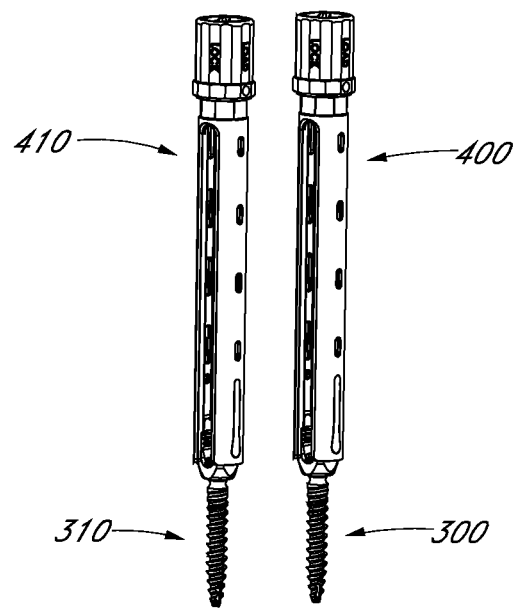
FIG. 11

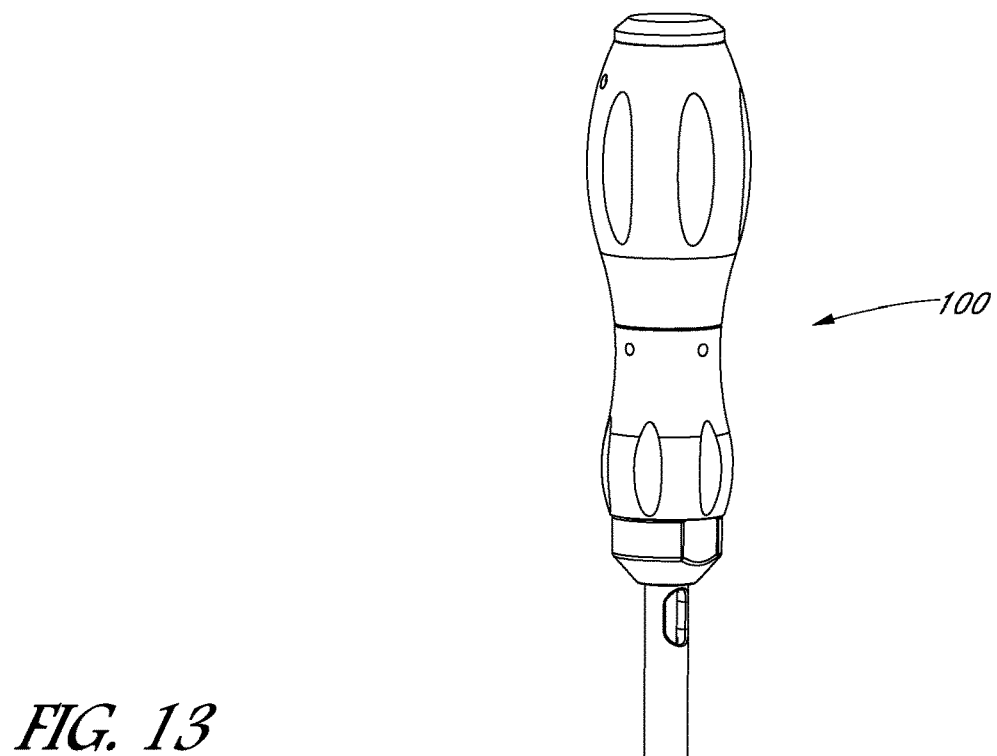
FIG. 13
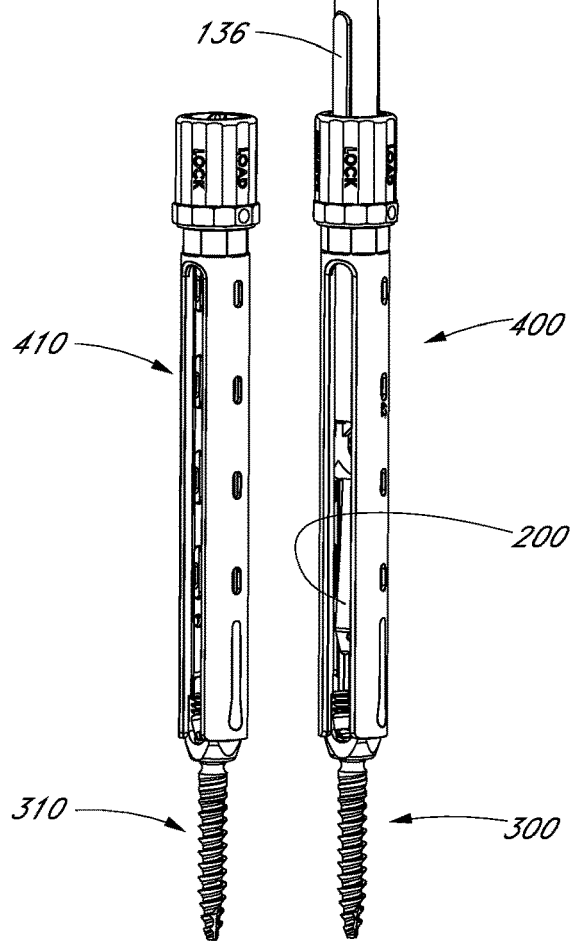

ARTICULATING ROD INSERTER

CROSS-REFERENCE TO RELATED APPLICATIONS

This application is a divisional of U.S. patent application Ser. No. 14/822,780, filed Aug. 10, 2015, now U.S. Pat. No. 9,750,546, which claims priority benefit to U.S. Provisional Application No. 62/036,053, filed Aug. 11, 2014, the disclosures of which are hereby incorporated by reference in their entireties.

BACKGROUND

Field

The present disclosure generally relates to the field of spinal orthopedics, and more particularly to a device for introducing a rod to a fixation system through a minimally invasive approach.

Related Art

The spine is a flexible structure that extends from the base of the skull to the tailbone. The weight of the upper body is transferred through the spine to the hips and the legs. The spine contains a plurality of bones called vertebrae. The vertebrae are hollow and stacked one upon the other, forming a strong hollow column for support. The hollow core of the spine houses and protects the nerves of the spinal cord. The spine is held upright through the work of the back muscles, which are attached to the vertebrae. While the normal spine has no side-to-side curve, it does have a series of front-to-back curves, giving it a gentle "S" shape.

Each vertebra is separated from the vertebra above or below by a cushion-like, fibrocartilage called an intervertebral disc. The discs act as shock absorbers, cushioning the spine, and preventing individual bones from contacting each other. In addition, intervertebral discs act as a ligament that holds vertebrae together. Intervertebral discs also work with the facet joint to allow for slight movement of the spine. Together, these structures allow the spine to bend, rotate and/or twist.

The spinal structure can become damaged as a result of degeneration, dysfunction, disease and/or trauma. More specifically, the spine may exhibit disc collapse, abnormal curvature, asymmetrical disc space collapse, abnormal alignment of the vertebrae and/or general deformity, which may lead to imbalance and tilt in the vertebrae. This may result in nerve compression, disability and overall instability and pain. If the proper shaping and/or curvature are not present due to scoliosis, neuromuscular disease, cerebral palsy, or other disorder, it may be necessary to straighten or adjust the spine into a proper curvature with surgery to correct these spinal disorders.

Fixation is a surgical method wherein two or more vertebrae are held together by the placement of implants to stabilize the vertebrae. Surgical treatments may involve manipulation of the spinal column by attaching corrective implants, such as rods, wires, hooks, screws, and the like, to straighten abnormal curvatures, appropriately align vertebrae of the spinal column and/or reduce further rotation of the spinal column. The correct curvature can be obtained by manipulating the vertebrae into their proper position and securing that position with a rigid system of screws and rods. The screws can be inserted into the pedicles of the vertebrae to act as bone anchors, and the rods may be inserted into heads of the screws. Two rods may run substantially parallel to the spine and secure the spine in the desired shape and curvature. Thus the rods, which are shaped to mimic the correct spinal curvature, force the spine into proper alignment.

In many cases, the fixation is augmented by a process called fusion, whereby an interbody implant is positioned in the intervertebral space between two or more vertebrae to join the vertebrae together. Bone grafts can be placed between the vertebrae and aid in fusion of the individual vertebrae together to form a correctly aligned spine.

In addition, minimally invasive surgical techniques have been used on the spine to access the spine through small incisions. Minimally invasive spine surgery offers multiple advantages as compared to open surgery. The advantages may include minimal tissue damage, minimal blood loss, smaller incisions and scars, minimal post-operative discomfort, and relative quick recovery time and return to normal function.

SUMMARY

An aspect of at least one of the embodiments disclosed herein includes a rod inserter for delivering a spinal fixation rod through an access channel, the rod inserter including a first member having an elongate tube with a proximal end and a distal end, with a passage extending from the proximal end to the distal end. The rod inserter includes a second member having an elongate shaft configured to move along the passage of the first member and a third member having a first end and a second end, the first end coupled to the second member. The rod inserter further includes a rod holder having a leading end coupled to the distal end of the first member and a trailing end coupled to the second end of the third member, the rod holder configured to transition from an aligned configuration, wherein a longitudinal axis of the rod holder is generally parallel with a longitudinal axis of the second member, to an angled configuration wherein the longitudinal axis of the rod holder is at an angle to the longitudinal axis of the second member, the rod holder configured to releasably couple with a rod. An actuator toward the proximal end of the first member can be configured to translate the second member, wherein translation of the second member transitions the rod holder between the aligned configuration and the angled configuration.

The rod holder can automatically release the rod when the rod holder is transitioned toward the aligned configuration. In some embodiments, the rod holder has a protrusion configured to be received by a complementary cutout on the rod.

The rod holder can include a mechanism for changing the rod holder between a clamping configuration and a release configuration. The second member can have a longitudinal channel for accessing the mechanism from the proximal end with a drive tool.

In some embodiments, the actuator is a rotating handle. The rotating handle can have threads that engage complementary threads on the second member to move the second member longitudinally.

The rod inserter can have an indicator corresponding to the orientation of the rod holder relative to the second member. In some embodiments, the rod inserter has an alignment feature configured to cooperate with an access tower, the alignment feature configured to prevent rotation of the rod inserter about its longitudinal axis.

An aspect of at least another of the embodiments disclosed herein includes a rod inserter having a shaft extending between a proximal end and a distal end of the rod inserter, the shaft having a longitudinal axis and configured to move along the longitudinal axis. The rod inserter includes a rod holder toward the distal end configured to rotate from an aligned configuration wherein a longitudinal axis of the rod holder is generally parallel with the longitudinal axis of the shaft, to an angled configuration wherein the longitudinal axis of the rod holder is at an angle to the longitudinal axis of the shaft, the rod holder configured to releasably couple with a rod. An actuator toward the proximal end is configured to transition the rod holder between the aligned configuration and angled configuration.

In some embodiments, the rod holder has a leading end pivotally coupled to the distal end of the rod inserter and a trailing end coupled to the shaft. The shaft can be connected to the rod holder by one or more linkages.

The rod holder can automatically releases the rod when the rod holder is transitioned toward the aligned configuration. In some embodiments, the rod holder has a protrusion configured to be received by a complementary cutout on the rod.

The rod holder can include a mechanism for changing the rod holder between a clamping configuration and a release configuration. The shaft can have a longitudinal channel for accessing the mechanism from the proximal end with a drive tool.

In some embodiments, the actuator is a rotating handle. The rotating handle can have threads that engage complementary threads on the shaft to move the shaft longitudinally.

The rod inserter can have an indicator corresponding to the orientation of the rod holder relative to the shaft. In some embodiments, the rod inserter has an alignment feature configured to cooperate with an access tower, the alignment feature configured to prevent rotation of the rod inserter about its longitudinal axis.

An aspect of at least one of the embodiments disclosed herein includes a method of delivering a rod onto a fixation system, the method including providing a rod inserter having a rod holder configured to rotate from an aligned configuration wherein a longitudinal axis of the rod holder is generally parallel with a longitudinal axis of the rod inserter, to an angled configuration wherein the longitudinal axis of the rod holder is at an angle to the longitudinal axis of the rod inserter, and further providing a rod releasably coupled to the rod holder. The method can further include inserting the rod longitudinally through an access channel of a first anchoring device and activating an actuator on the rod inserter to transition the rod holder from the aligned configuration to the angled configuration, such that a trailing end of the rod is near the first anchoring device and a leading end of the rod is near a second anchoring device.

In some embodiments, the method further includes activating the actuator to transition the rod holder from the angled configuration to the aligned configuration, wherein the rod holder automatically releases the rod. The method can further include moving a mechanism that releases the rod from the rod holder.

The method can further include securing the rod to the first or second anchoring device. Securing the rod to the first or second anchoring device can include fastening a threaded cap onto the first or second anchoring device.

In some embodiments, the first and second anchoring devices are pedicle screws with heads adapted to receive the rod.

BRIEF DESCRIPTION OF THE DRAWINGS

Specific embodiments and modifications thereof will become apparent to those skilled in the art from the detailed description herein having reference to the figures that follow, of which:

FIG. 11 is a perspective view of the rod inserter of FIG. 1 positioned above pedicle screws with towers attached.

FIG. 13 is a perspective view of the rod inserter of FIG. 1 inserted into a tower and a leading end of the rod near the pedicle screw.

DETAILED DESCRIPTION

Devices and methods of fixing two or more vertebrae are disclosed herein and in some embodiments can involve minimally invasive techniques. Several non-limiting embodiments will now be described with reference to the figures, wherein like numerals reflect like elements throughout. The terminology used in the description presented herein is not intended to be interpreted in any limited or restrictive way, simply because it is being utilized in conjunction with a detailed description of certain specific embodiments. Furthermore, some embodiments may include several novel features, no single one of which is solely responsible for its desirable attributes or which is essential to the devices and methods described herein.

The words proximal and distal are applied herein to denote specific ends of components of the instrument described herein. A proximal end refers to the end of a component nearer to an operator of the instrument when the instrument is being used. A distal end refers to the end of a component further from the operator and extending towards the surgical area of a patient and/or the implant. The words top, bottom, left, right, upper and lower are used herein to refer to sides of the device from the described point of view. These reference descriptions are not intended to limit the orientation of the implant tool and the device can be used in any functional orientation.

Figure 1:
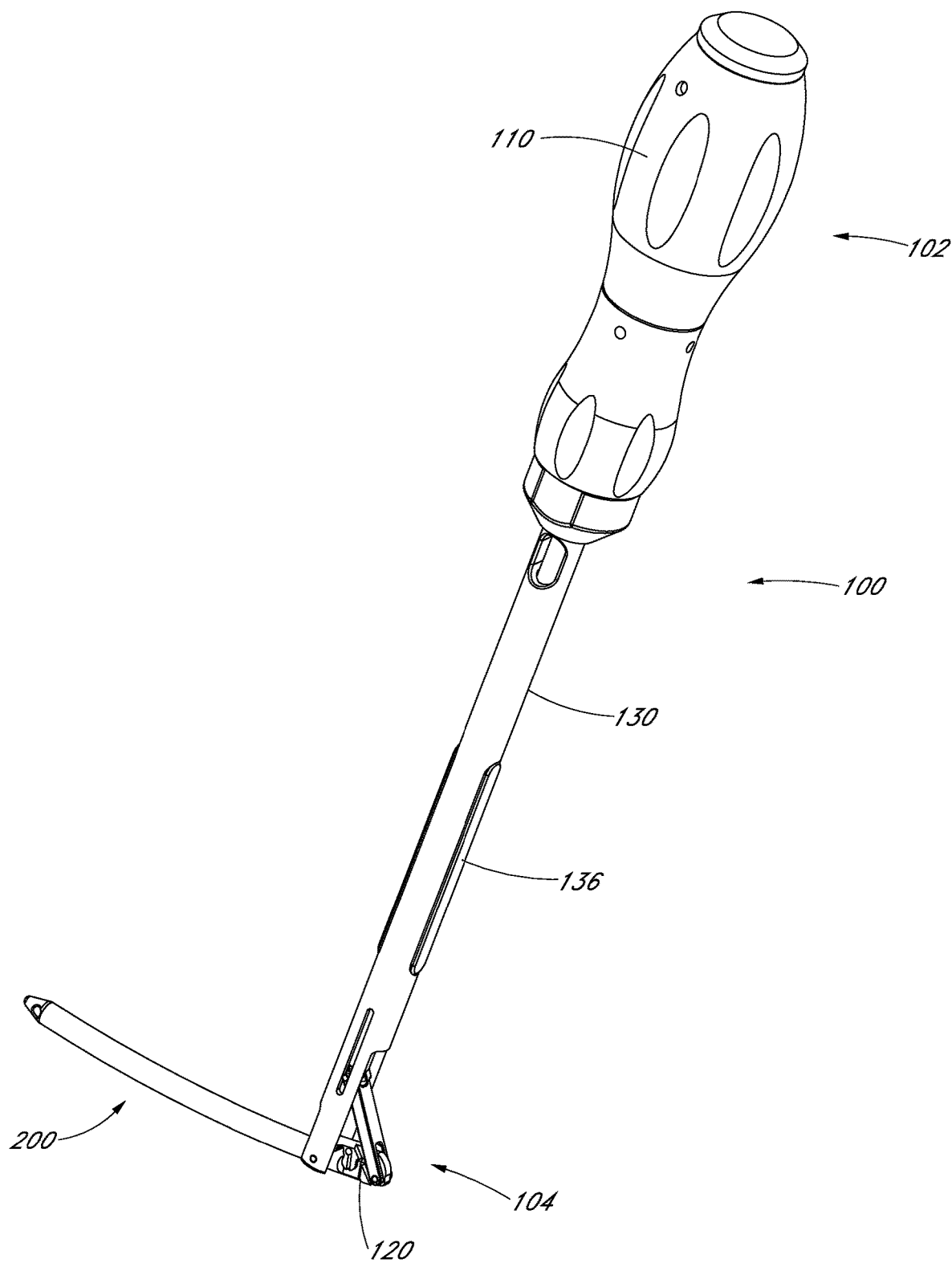
FIG. 1 is a perspective view of a rod inserter with a rod attached, according to an embodiment of the present disclosure.
Figure 2:
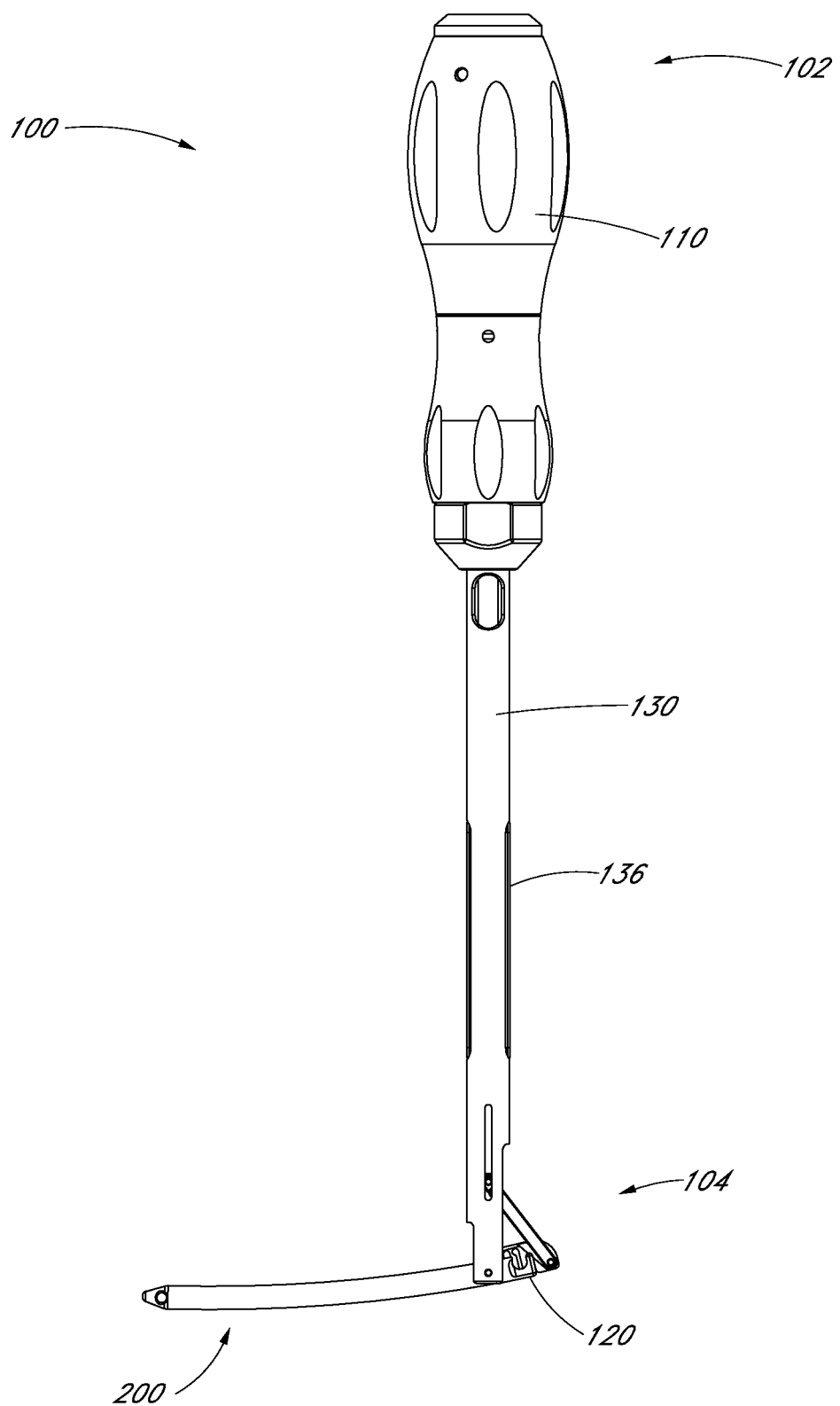
FIG. 2 is a side view of the rod inserter and rod of FIG. 1.

FIGS. 1 and 2 illustrate a rod inserter 100 having a rod 200 attached. The illustrated rod inserter 100 is an elongate tool used to deliver, and in some situations reduce, a rod onto a spinal fixation system. The rod inserter 100 has a proximal end 102 and a distal end 104. The proximal end 102 can have a handle 110 and the distal end 104 can have a rod holder 120 that is configured to releasably couple with the rod 200. An elongate tube 130 can extend from the handle 110 to the rod holder 120. An alignment feature 136 can be disposed on the rod inserter 100 to help with proper orientation of the rod inserter 100 during insertion into the towers, as described below.

Figure 3:
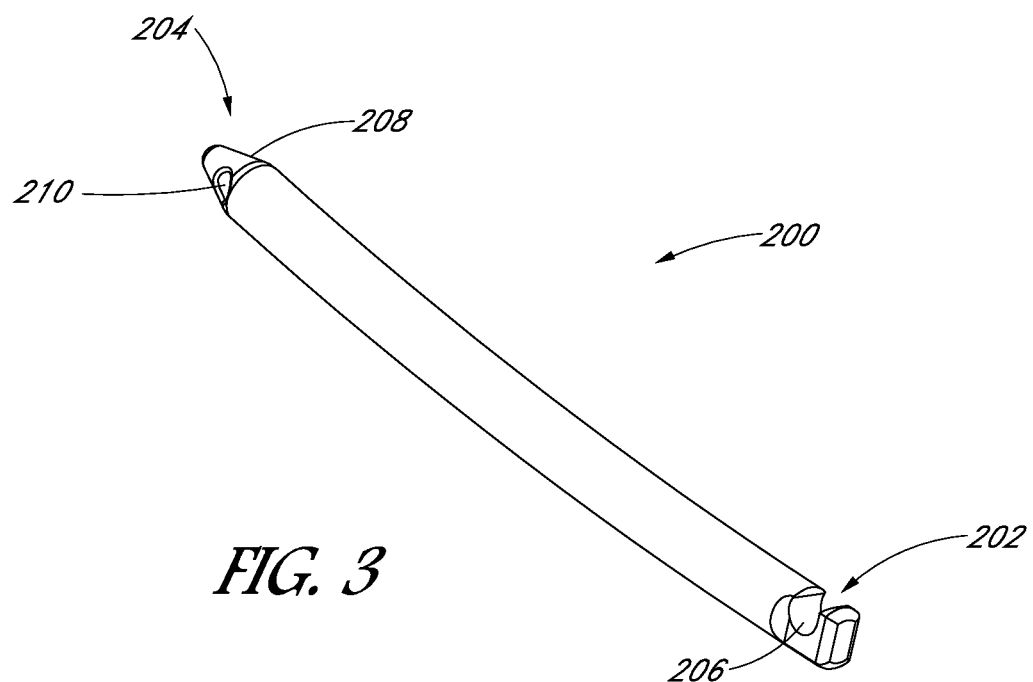
FIG. 3 is a perspective view of the rod of FIG. 1.
Figure 4:
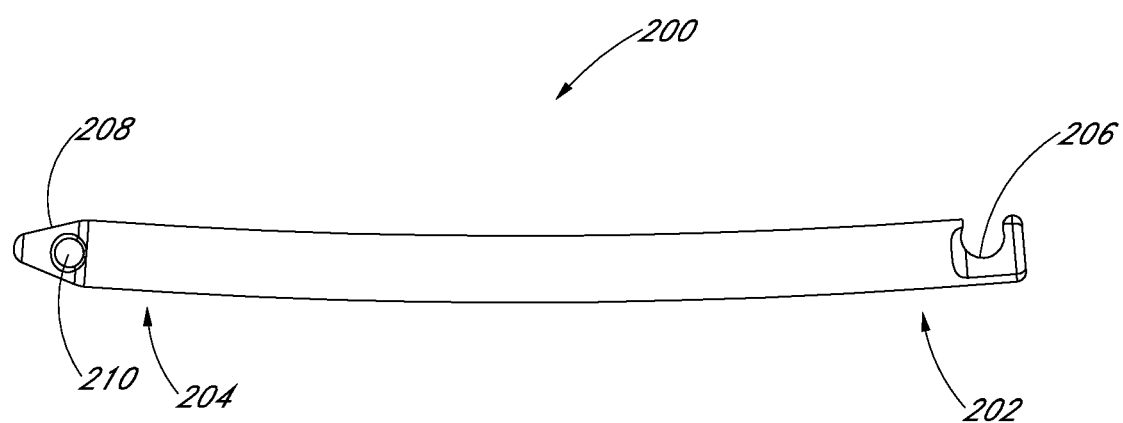
FIG. 4 is a side view of the rod of FIG. 3.

As illustrated in FIGS. 3 and 4, the rod 200 can be an elongate member configured to extend between two or more bone anchors that are fixed to two or more vertebrae. In the illustrated embodiment, the rod 200 has an elongate cylindrical shape with a trailing end 202 and a leading end 204. In other embodiments, the rod can have other shapes, such as elongate members with an oval, square, rectangular, or polygonal cross-sectional shape. The illustrated rod 200 has a slight bend or curve, which may help the fixation system to preserve the natural shape of the spinal anatomy. In other embodiments, the rod can be substantially straight, have a greater curve than the illustrated embodiment, or have multiple bends.

Figure 5:
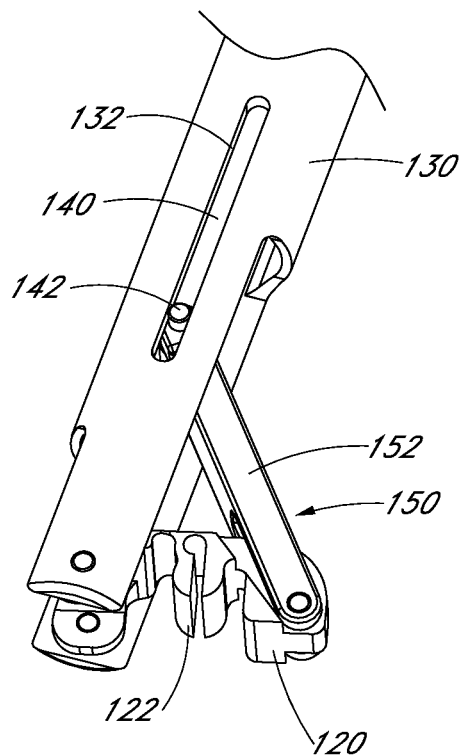
FIG. 5 is a close-up perspective view showing the rod holder of the rod inserter of FIG. 1 without a rod.

The trailing end 202 of the rod 200 can have a coupling feature to accept a complementary feature on the rod holder 120. For example, the illustrated rod 200 has a cutout 206 with a round shape that is complementary to the shape of a protrusion 122 or clip on the rod holder 120, as shown in FIG. 5. The protrusion 122 can have a slot through the middle that allows the sides of the protrusion to deflect in order to release from the cutout 206 of the rod 200. In some embodiments, the protrusion can have a different release design, such as the protrusion being made of a compressible material that compresses to release from the cutout. The protrusion 122 can be customized so that it releases from the rod 200 at a predetermined amount of separation force. In other embodiments, the coupling feature between the rod and rod holder can be any functional coupler that disconnects with a predetermined amount of separation force. The position of the protrusion 122 on the rod holder 120 can be tailored so that the rod has a predetermined amount of overhang from the fixation device when implanted. The amount of overhang can be selected for optimized efficacy.

A first end of the rod holder 120 is hingedly coupled to the distal end of the tube 130. A second end of the rod holder 120 is hingedly coupled to a distal end of a linkage 150. In the illustrated embodiment, the hinged couplings comprise pins. In other embodiments, the hinged coupling can be any functional hinge, such as screws, ball and sockets, bending joints, friction connections, and the like.

With continued reference to FIG. 5, the linkage 150 in the illustrated embodiment comprises two struts 152 attached to either side of the rod holder 120, leaving space between the struts 152 to accommodate the rod holder 120 when rotated. A middle piece can be disposed between the two struts 152 for increased structural strength. In some embodiments, the linkage 150 can be a single component with a forked distal end to accommodate the rod holder. The proximal end of the linkage 150 is hingedly coupled to a distal end of a shaft 140. The hinged coupling can include pins or other functional coupler, as discussed above. The shaft 140 is an elongate member that extends through the middle of the tube 130 to transition the rod holder, and thus the rod, from an aligned configuration to an angled configuration, as discussed further below.

Figure 6:
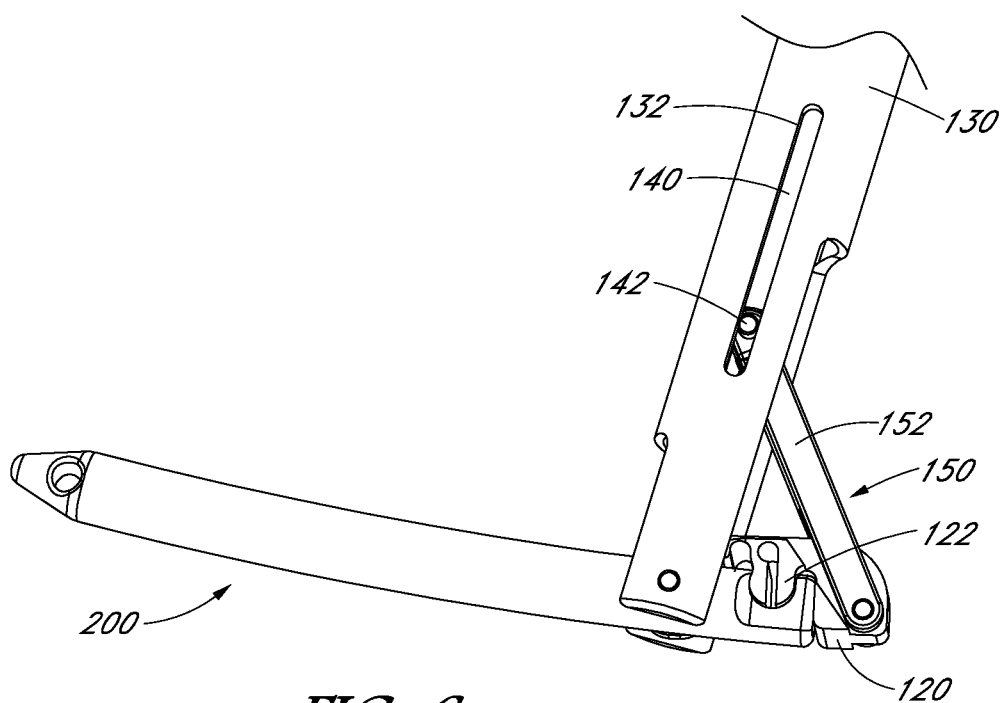
FIG. 6 is a close-up perspective view showing the rod holder of the rod inserter of FIG. 1 with a rod attached.

With reference to FIG. 6, the rod 200 can be releasably coupled with the rod holder 120 such that the rod 200 can be automatically separated from rod inserter 100. As used herein, automatically separated means separation without directly releasing the rod 200. For example, when the rod is secured to the fixation system and the rod holder 120 is retracted, the rod holder 120 and rod 200 are pulled apart until the protrusion 122 is separated from the cutout 206. The rod 200 is released automatically as a result of the retraction of the rod holder 120, without having to directly uncouple the rod 200 or have a secondary release mechanism.

In some embodiments, the rod and rod holder can have other suitable shapes or configurations that allow releasable attachment of the rod to the rod holder. For example, the rod 200 and rod holder 120 can be releasably attached with adhesives, clips, magnets, snaps, compression joints or other suitable releasable connections. In some embodiments, the cutout can be disposed on the rod holder and the protrusion can be disposed on the rod.

The leading end 204 of the rod 200 can be bulleted with an angled surface 208 to help the rod move through the patient's tissue and muscle. Preferably, the tip of the leading end 204 is blunt to minimize trauma to the surrounding tissue as the rod 200 is positioned onto the bone anchors. The leading end 204 can have a hole 210 that helps visualize the rod 200 during the implantation procedure, such as when using X-ray or fluoroscopic imaging techniques. The hole 210 can produce a contrasting image compared to the surrounding rod so that surgeons can visualize the location of the leading end 204. In some embodiments, the rod can include radiopaque markers (e.g., tantalum, titanium, etc.) that can be seen in X-ray or other imaging techniques.

Figure 7:
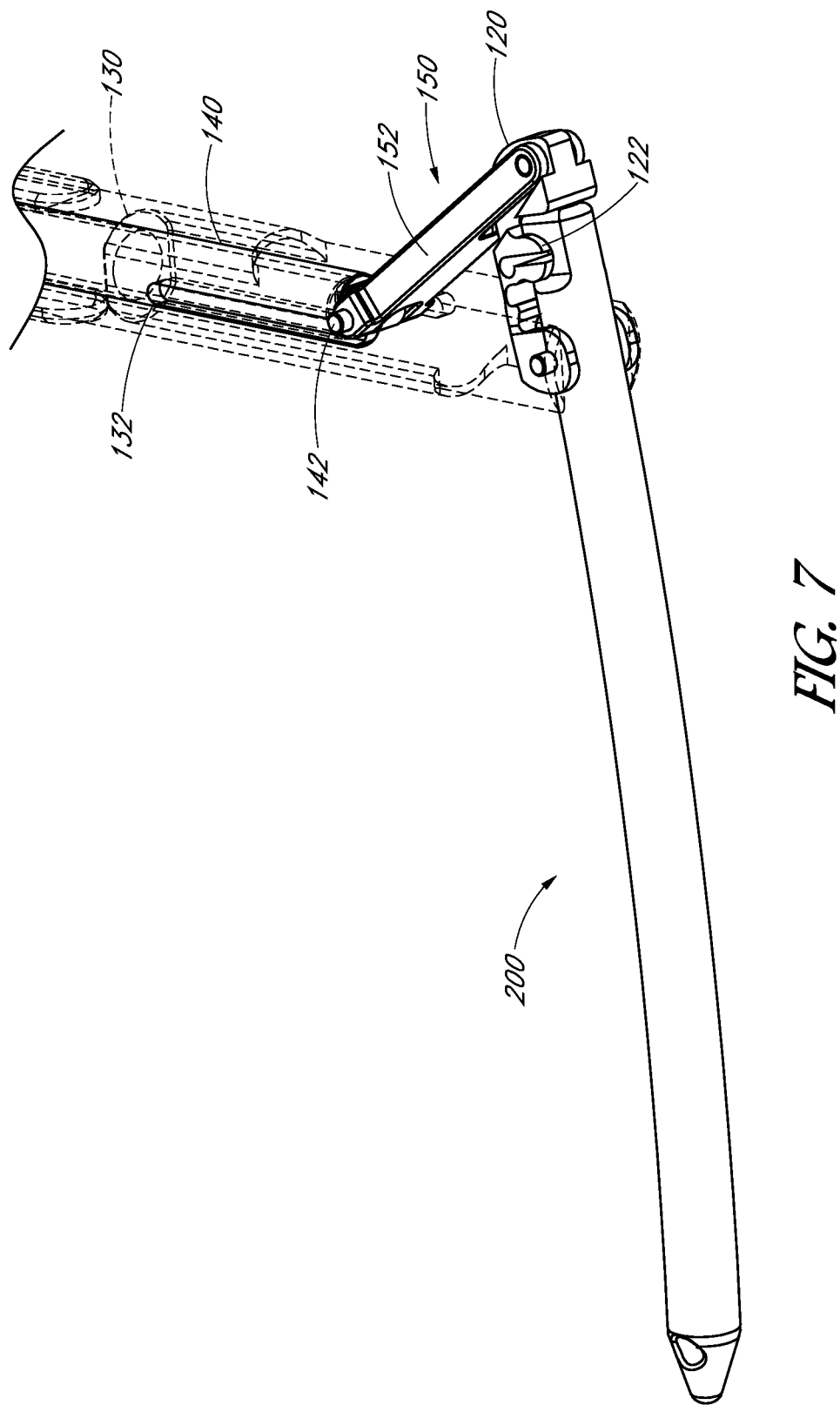
FIG. 7 is a close-up perspective view showing the rod holder of the rod inserter of FIG. 1 with a rod attached, shown with portions of the rod inserter as transparent.

FIG. 7 illustrates the distal end 104 of the rod inserter 100 with the tube 130 shown as transparent. The shaft 140 is shown extending through the middle of the tube 130. The proximal end of the shaft 140 is coupled to an actuator on the handle and the shaft 140 is configured to slide longitudinally through the tube 130 when the actuator is activated. As the shaft 140 moves along the longitudinal direction, the shaft 140 pushes the proximal end of the linkage 150, causing the distal end of the linkage 150 to pivot out at least partially in the lateral direction, transitioning the rod holder 120 between an aligned configuration and an angled configuration, as described in further detail below.

The shaft 140 can be configured to move in the longitudinal direction, but constrained from rotating about the longitudinal axis. In the illustrated embodiment, the shaft 140 and the linkage 150 are rotatably connected with a pin 142. The pin 142 extends beyond the connection between the shaft 140 and linkage 150 and through a slot 132 in the tube 130. The slot 132 is an elongate cutout extending longitudinally in the side walls of the tube 130. As the actuator is activated, the shaft 140 can be constrained from rotating by the pin 142 in the slot 132, but allowed to move longitudinally along the length of the slot 132. In other embodiments, the shaft 140 may have a separate protrusion or pin apart from pin 142 that is configured to slide within the slot 132. In some embodiments, the shaft can have other configurations that permit longitudinal movement and constrain rotational movement. For example, the shaft can have a non-circular cross-sectional shape, such as an oval, square, or polygon, and the inner cavity of the tube can have a complementary shape, such that the tube blocks rotation of the shaft.

Figure 8:
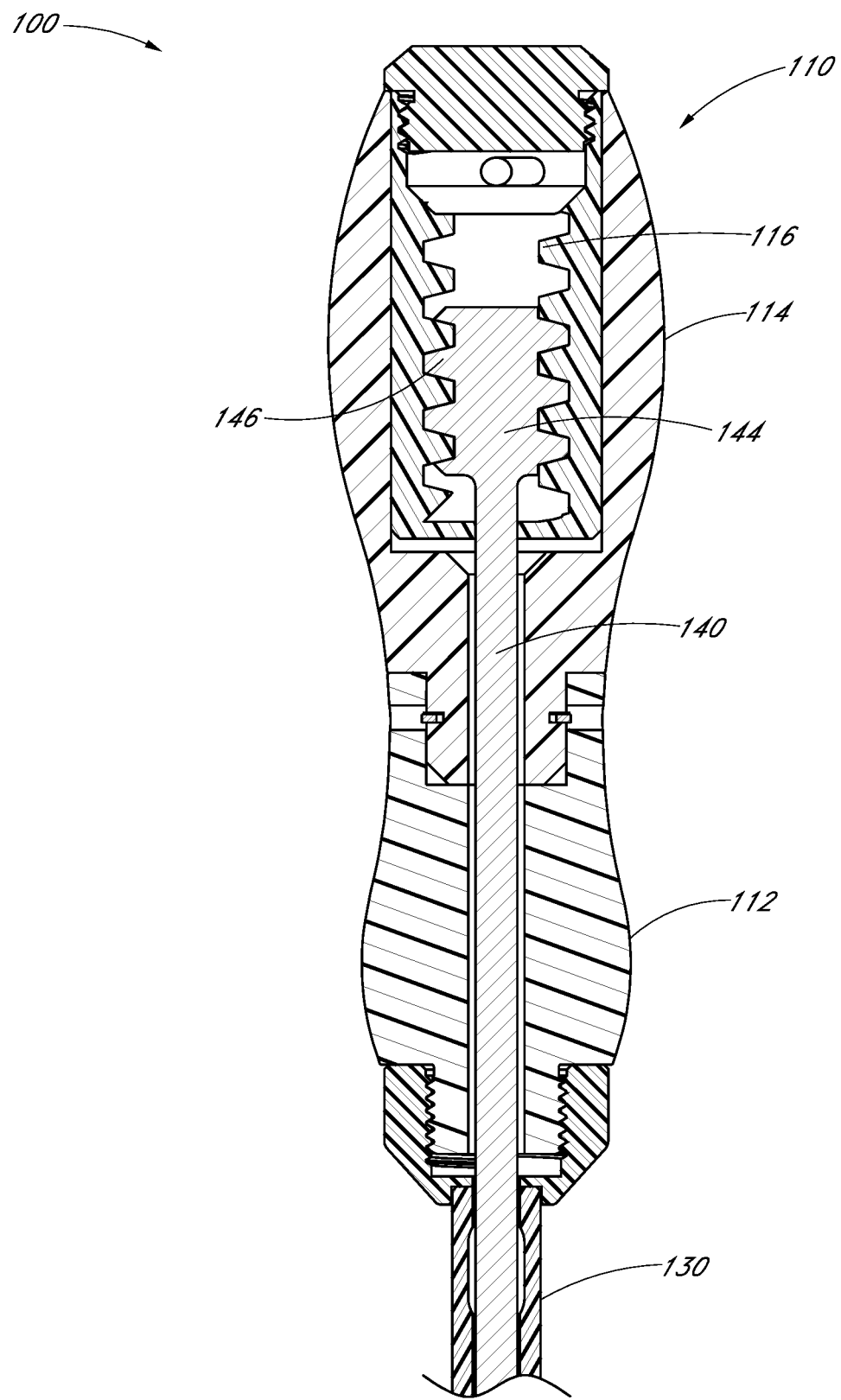
FIG. 8 is a cross-sectional side view of the proximal end of the rod inserter of FIG. 1.

FIG. 8 illustrates a cross-sectional view of the proximal portion of a rod inserter 100 according to some embodiments. The handle 110 can comprise a fixed portion 112 and an actuator portion 114. The fixed portion 112 is rigidly connected to the tube 130 and the actuator portion 114 can rotate or otherwise move relative to the fixed portion 112. The actuator portion 114 can be activated to drive the shaft 140 in the longitudinal direction. In the illustrated embodiment, the shaft 140 has a proximal end 144 that is engageable with the actuator portion 114 of the handle 110. For example, the proximal end 144 of the shaft 140 can have external threads 146 that engage with internal threads 116 on the actuator portion 114. When the illustrated actuator portion 114 is rotated, the internal threads 116 cooperate with the external threads 146 of the proximal end 144 to move the proximal end 144 and the shaft 140 in the proximal-distal direction. As mentioned above, the shaft 140 can be constrained from rotating by the pin 142 in the slot 132, but allowed to move longitudinally along the length of the slot 132. In other embodiments, the proximal portion of the rod inserter can have other actuation mechanisms for translating the shaft 140, such as a ratcheting handle or a trigger style mechanism or any other suitable translation mechanism.

Figure 9:
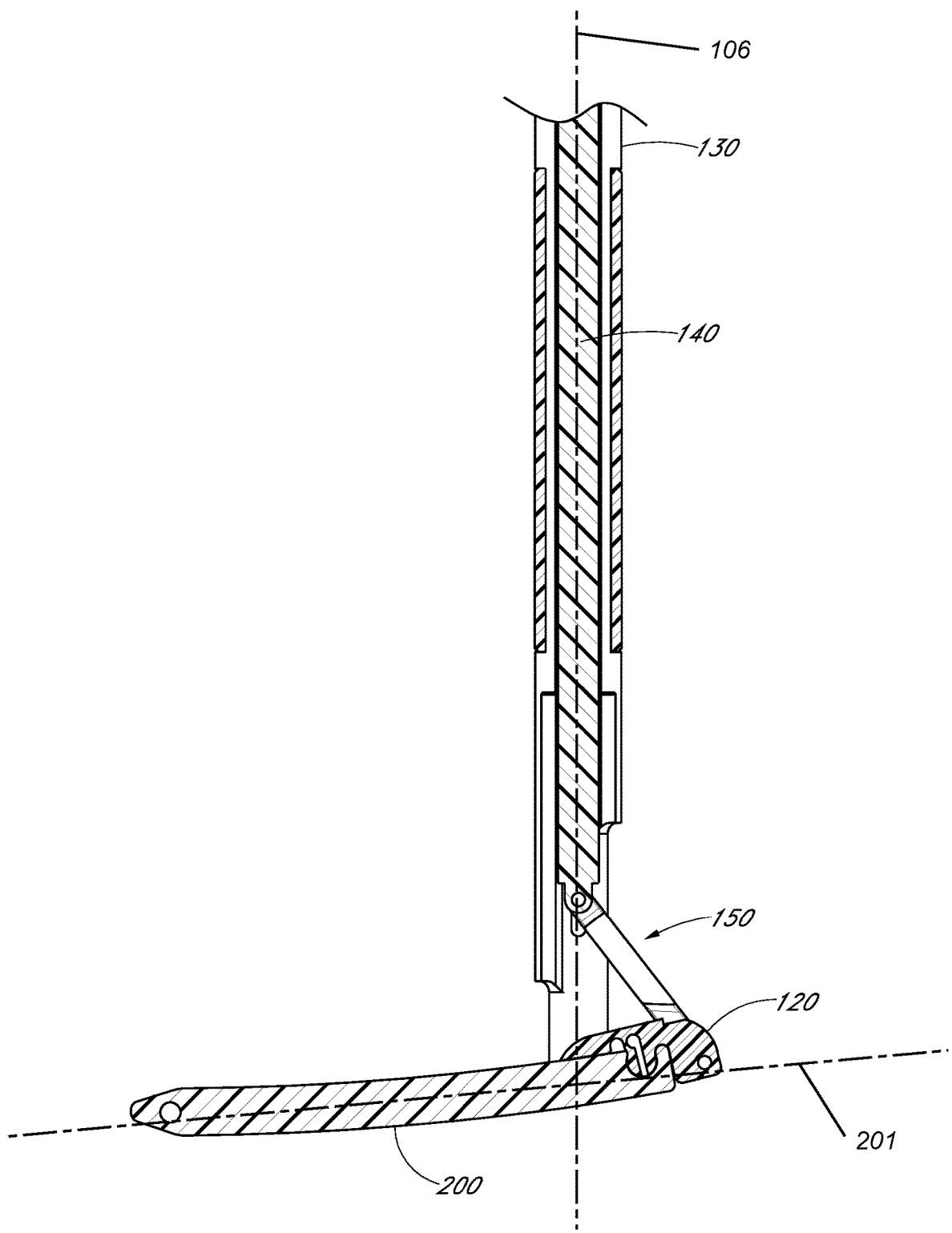
FIG. 9 is a cross-sectional side view of the distal end of the rod inserter and rod of FIG. 1.

With reference to FIG. 9, the shaft 140 can be moved in the proximal-distal direction to transition the rod 200 between an aligned configuration, wherein the longitudinal axis 201 of the rod 200 and the longitudinal axis 106 of the rod inserter 100 are generally aligned, to an angled configuration, wherein the longitudinal axis 201 of the rod 200 is at an angle to the longitudinal axis 106 of the rod inserter 100. As the actuator portion 114 of the handle 110 shown in FIG. 8 is activated, the shaft 140 moves in the longitudinal direction and acts upon the proximal end of the linkage 150. When the shaft 140 is moved in the distal direction, the proximal end of the linkage 150 also moves in the distal direction causing the distal end of the linkage 150 to swing out laterally. The distal end of the linkage 150 is attached to the second end of the rod holder 120, which also swings out laterally, transitioning the rod holder 120 from an aligned configuration to an angled configuration shown in FIG. 9. Since the rod 200 is releasably coupled to the rod holder 120, the rod 200 is also transitioned from an aligned configuration to an angled configuration by activating the actuator portion 114 of the handle 110.

Figure 10:
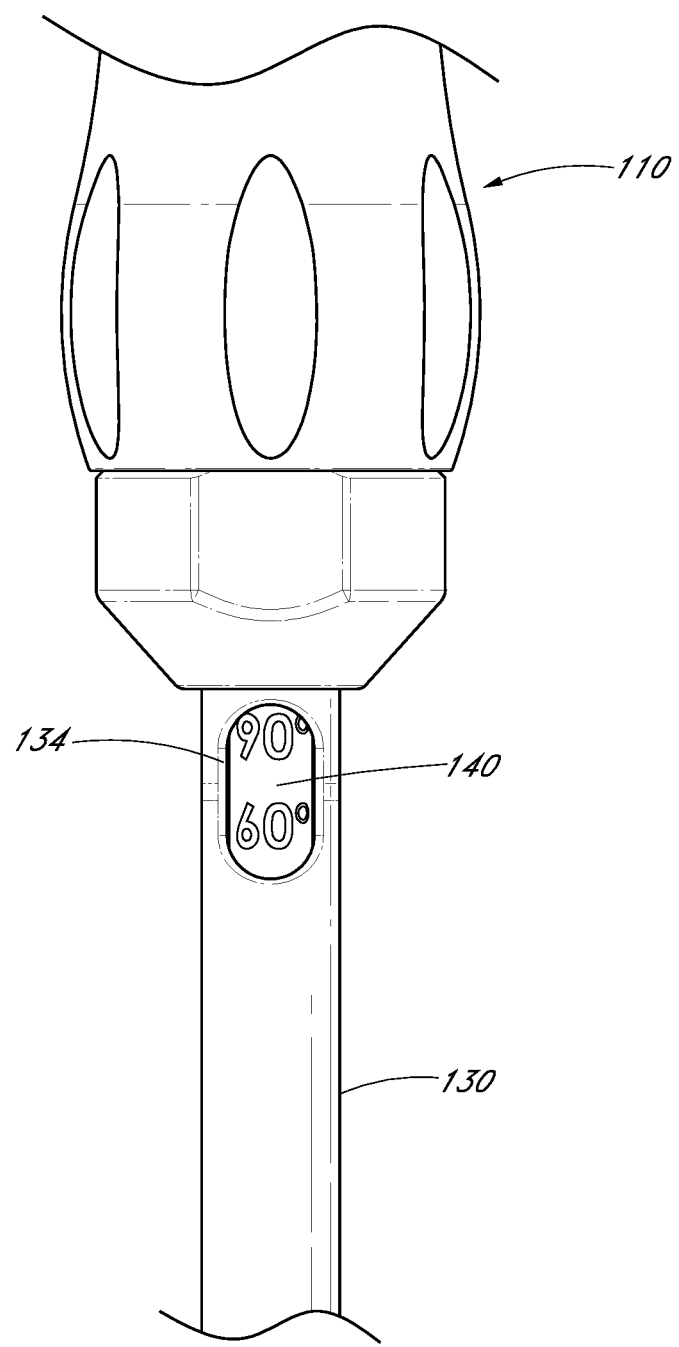
FIG. 10 is a close-up side view of the rod inserter of FIG. 1 showing an angle indicator window.

As illustrated in FIG. 10, in some embodiments, the tube 130 can have a window 134 with a display that indicates the position of the rod 200. The window 134 is configured to be visible from outside the incision so that the surgeon can know the orientation of the rod 200 without directly viewing inside the implant site. For example, the shaft 140 can be marked along the longitudinal length with angle indicators that correspond to the angle of the rod 200 relative to the tube 130. As the shaft 140 moves in the longitudinal direction, the indicated angle displayed through the window changes with the angle of the rod 200. The indicated angle can start from 0 degrees, indicating that the rod 200 is generally longitudinally aligned with the tube 130, to about 90 degrees, indicating that the rod 200 is generally perpendicular to the tube 130. In some embodiments, the indicated angle can go higher than 90 degrees, indicating that the rod 200 is oriented beyond perpendicular to the tube 130. In other embodiments, the display can simply be sequential numbers, letters, symbols, or other markings that indicate the orientation of the rod.

In a method of using the rod inserter 100, the vertebral column is accessed and one or more vertebrae are identified and accessed. In some embodiments, the upper cervical spine is accessed. In other embodiments, the lower cervical spine, cervicothoracic junction, thoracic spine, thoracolumbar junction, lumbar region, lumbosacral junction, sacrum or combination of the above regions are accessed. Two or more vertebrae are accessed and in some embodiments, two or more adjacent vertebrae are accessed.

In a minimally invasive technique, the vertebrae can be accessed through two small incisions that are made near the selected vertebrae. The incisions can be just large enough to accommodate access cannulas or towers. In some embodiments, the vertebral column can be accessed through an incision that is large enough to access the two or more vertebrae in an open procedure.

With reference to FIG. 11, a first pedicle screw 300, or other anchoring device, can be implanted in a first vertebra. A first tower 400 can be attached to the pedicle screw 300 before being implanted or after implantation. A second pedicle screw 310, or other anchoring device, can be implanted in a second vertebra. A second tower 410 can be attached to the second pedicle screw 310 before being implanted or after implantation. The towers 400, 410 can be elongate tubes or cannulas with an inner channel through which devices and instruments can be inserted to reach the pedicle screws 300, 310 from a remote proximal location outside the incision. The pedicle screws can have threaded shanks that are configured to be screwed into and retained by vertebral bone. The heads of the pedicle screws can be configured to accept a rod. For example, the illustrated embodiment of the pedicle screw heads include a U-shaped structure with internal threads, wherein the rod is held in the U-shaped cutout and retained by a threaded cap or a nut with external threads.

After the two or more pedicle screws are implanted in the vertebrae, the rod inserter 100 with the rod 200 attached can be positioned above one of the towers. In the embodiment illustrated in FIG. 11, the rod 200 is generally longitudinally aligned with the rod inserter 100 in preparation for insertion in the first tower 400. The rod inserter 100 is oriented such that the rod 200 can be angled toward the second tower 410. In some embodiments, the rod inserter 100 can have alignment features 136 that engage with features on the towers to help orient the rod inserter 100 in the desired direction. In the illustrated embodiment, the alignment features 136 are protrusions on the tube 130 that are inserted into longitudinal slots on the towers. The illustrated embodiment has two elongate protrusions on opposite sides of the rod inserter 100, however, in other embodiments the alignment feature can be any suitable feature, such as directional indicators on the handle 110 tip or tube 130.

Figure 12:
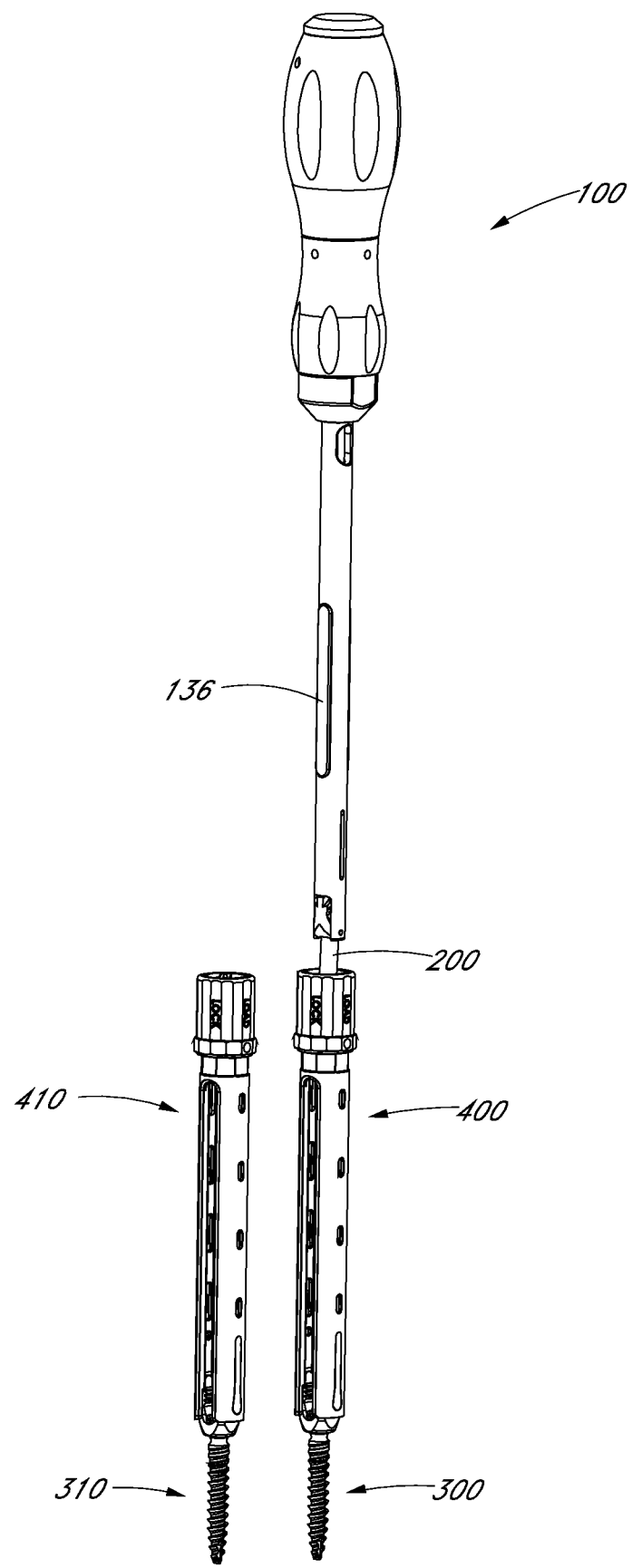
FIG. 12 is a perspective view of the rod inserter of FIG. 1 being inserted into a tower.
Figure 14:
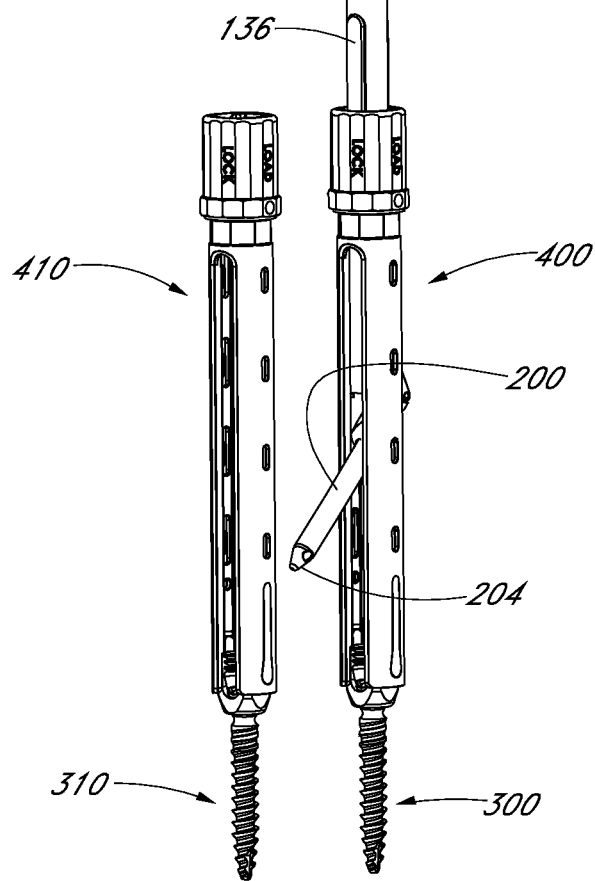
FIG. 14 is a perspective view of the rod inserter of FIG. 1 inserted into a tower and being actuated to move the rod partially toward a second tower.

FIG. 12 illustrates the rod 200 being inserted into the first tower 400. The rod 200 is generally longitudinally aligned with the first tower 400 as it is inserted into the tower 400. FIG. 13 illustrates the rod 200 and rod inserter 100 advanced further down the first tower 400. The alignment feature 136 is coupled with slots in the tower 400, which helps orient the rod inserter 100 in the proper direction for advancing the rod 200 to the second tower 410. The alignment feature 136 can also help prevent the rod 200 from being inadvertently misaligned or rotated about the longitudinal axis of the tower 400. The rod 200 is shown nearing the bottom of the first tower 400 and top of the first pedicle screw 300. As the rod 200 approaches or reaches the top of the first pedicle screw 300, the actuator portion 114 of the handle 110 can be activated (e.g., rotated) to start angling the rod 200 relative to the longitudinal axis of the first tower 400 and rod inserter 100, as illustrated in FIG. 14. The leading end 204 of the rod 200 can move out of the tower 400 through openings that are disposed on the sides of the towers.

Figure 15:
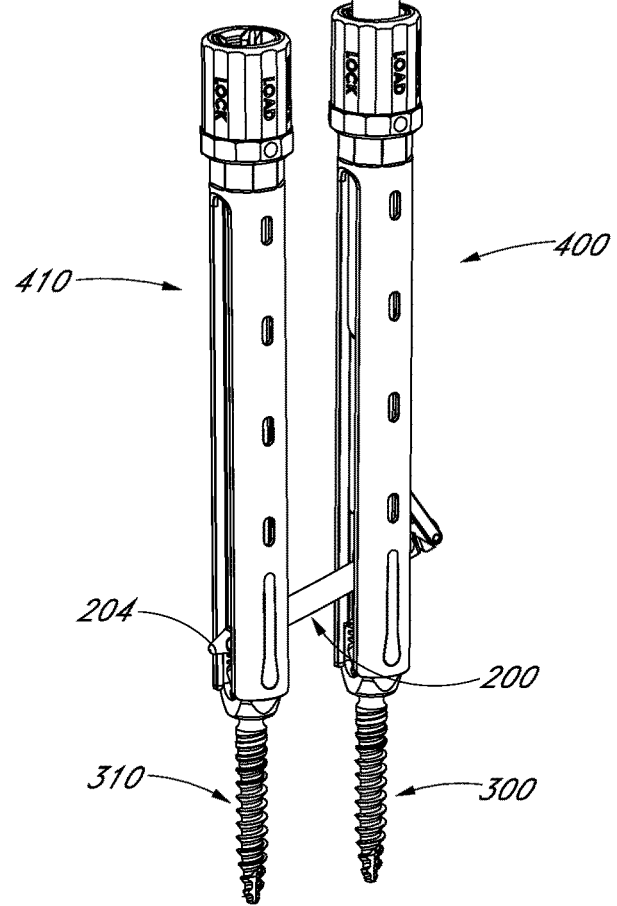
FIG. 15 is a perspective view of the rod inserter of FIG. 1 inserted into a tower and a leading end of the rod positioned in a second tower.

With reference to FIG. 15, as the actuator portion 114 is further activated, the leading end 204 of the rod 200 continues to move toward the second tower 410. The rod inserter 100 can be moved further distally down the first tower 400 as the rod 200 is angled relative to the tube 130. The leading end 204 of the rod 200 can move through openings in the second tower 410 and through the channel of the second tower 410.

Figure 16:
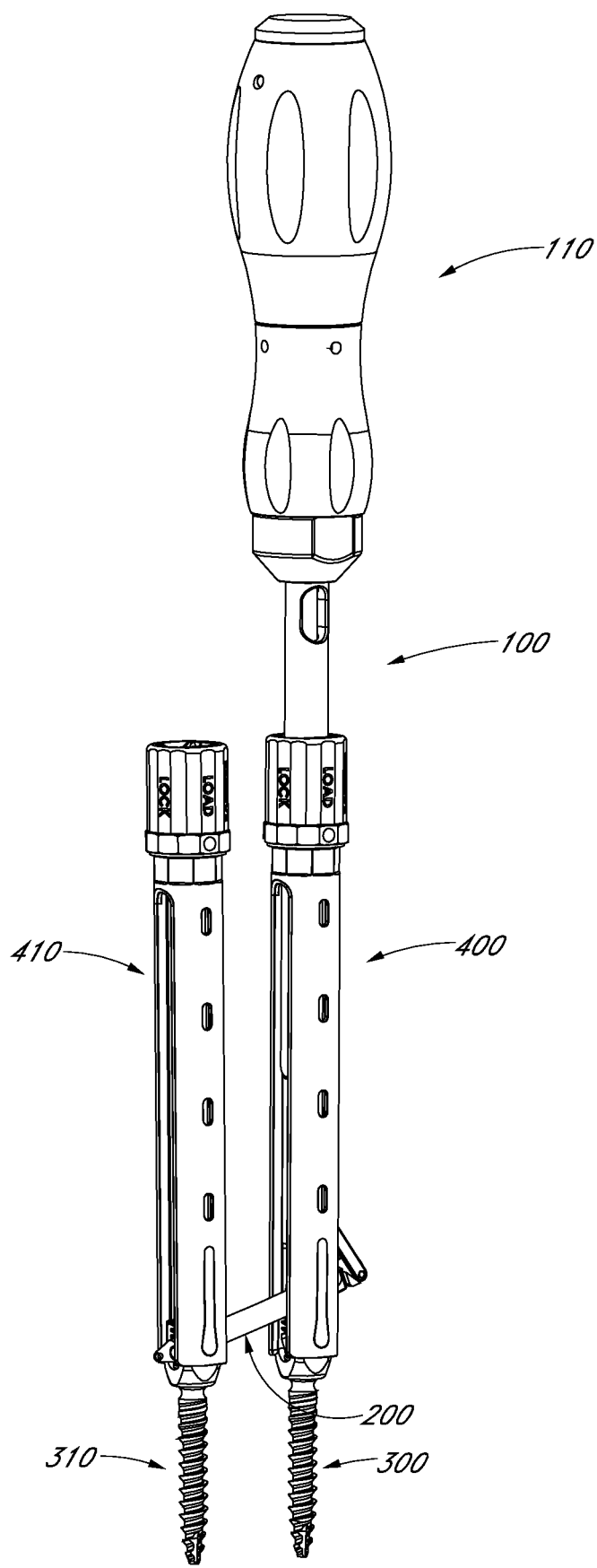
FIG. 16 is a perspective view of the rod inserter of FIG. 1 inserted into a tower and the rod extending between two towers.

FIG. 16 illustrates the rod 200 seated in the heads of the pedicle screws 300, 310. In the illustrated embodiments, the rod 200 is generally perpendicular to the tube 130, or generally parallel with the spinal column. In other embodiments, the rod 200 can be at other angles to suit the positions of the pedicle screws and/or anatomy of the patient. Advantageously, the amount of rod overhang from the pedicle screws can be controlled when using the rod inserter 100. When the rod 200 is generally perpendicular to the tube 130, a set length of the rod extends beyond the longitudinal axis of the rod inserter 100. This set length becomes the overhang from the pedicle screws once the rod 200 is attached to the pedicle screw. Therefore, a predetermined overhang can be achieved with the rod inserter 100 by tailoring the design of the rod holder 120 to control the set length that the rod 200 extends beyond the longitudinal axis of the rod inserter 100 when in the angled configuration.

Figure 17:
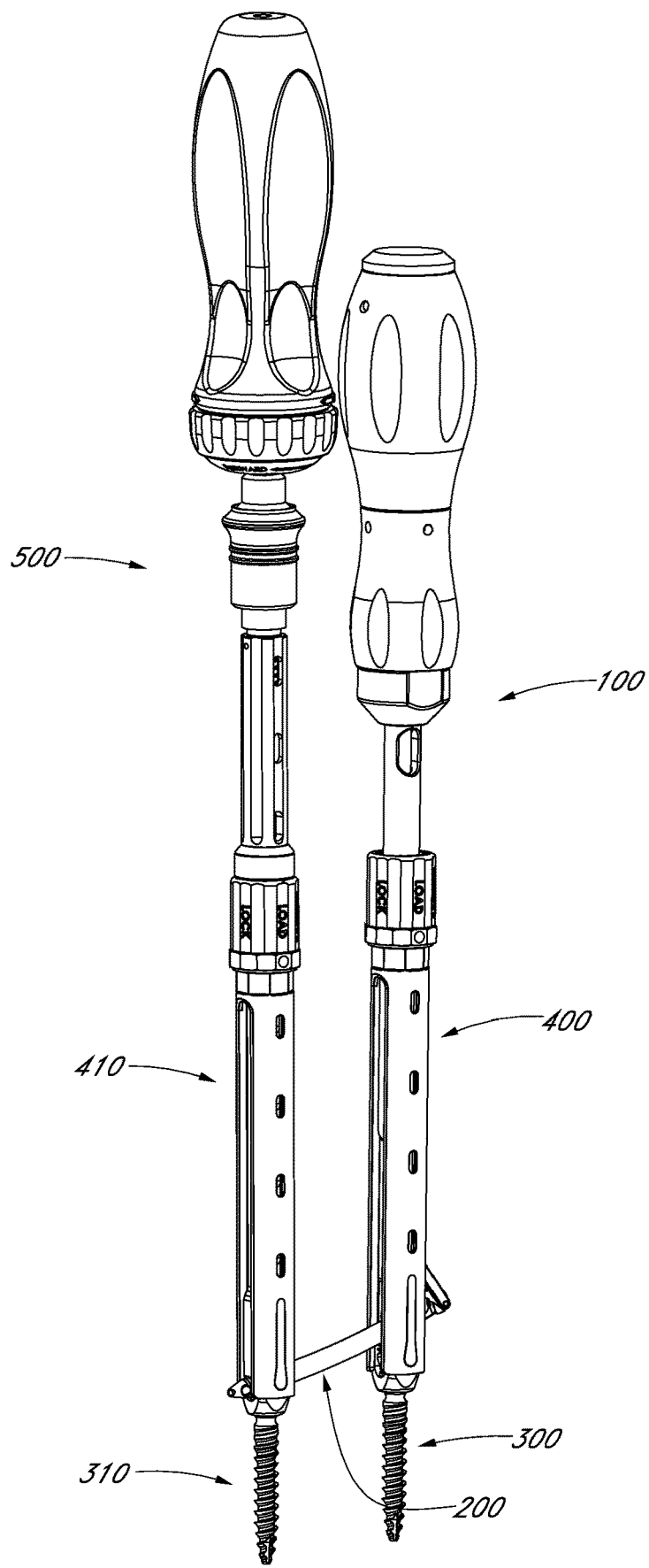
FIG. 17 is a perspective view of the rod inserter of FIG. 1 inserted into a tower and a fastener driver inserted into another tower.

FIG. 17 illustrates the rod inserter 100 in the first tower 400, and a fastener driver 500 and/or reducer in the second tower 410. The fastener driver 500 is an elongate tool that is configured for insertion through the tower to deliver and couple a fastener, such as a threaded cap, to the head of a pedicle screw. In the illustrated embodiment, the fastener driver 500 is positioned through the second tower 410 and a threaded cap is fastened to the second pedicle screw 310, which tightens against the rod 200 to fix the leading end 204 of the rod 200.

Figure 18:
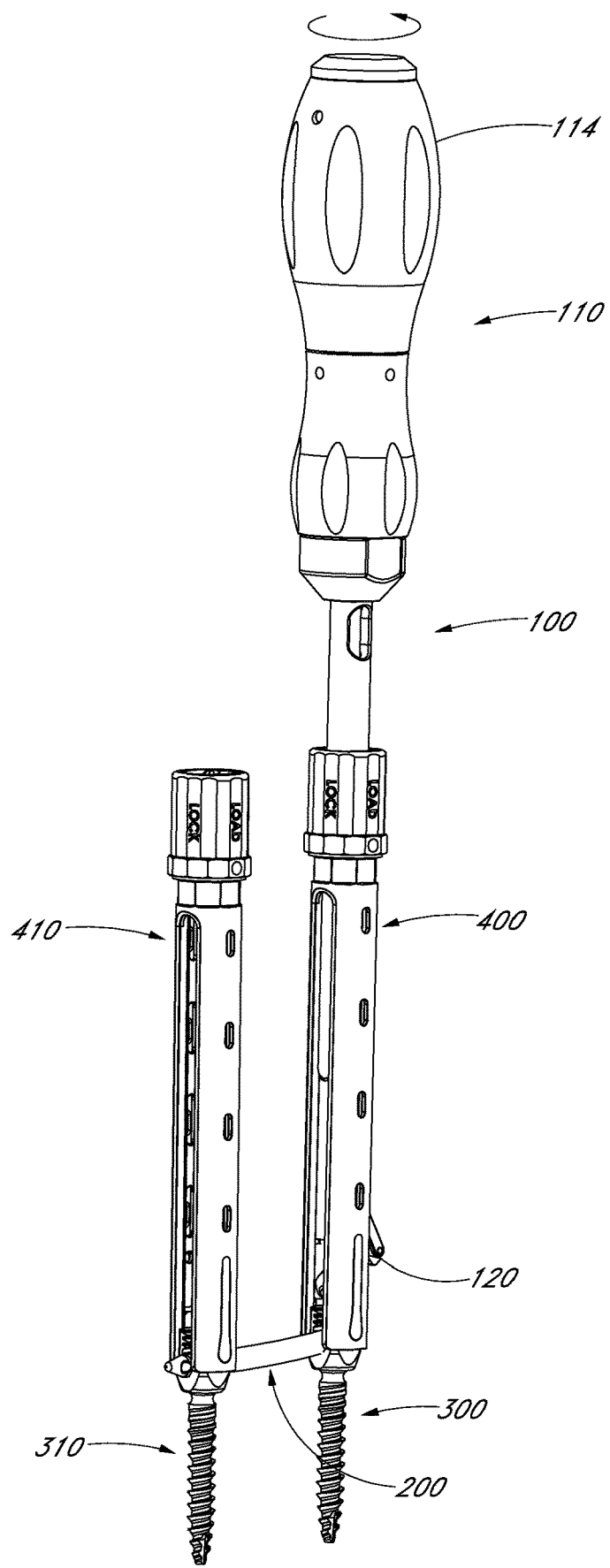
FIG. 18 is a perspective view of the rod inserter of FIG. 1 inserted into a tower and being actuated to retract the rod holder.

After the leading end 204 of the rod 200 is fixed to the second pedicle screw 310, the actuator portion 114 can be activated in reverse to retract the rod holder 120 back into the tube 130, as illustrated in FIG. 18. Since the rod 200 is held in place on the second pedicle screw by the threaded cap, other fastener or tool, when the rod holder 120 is retracted it separates from the rod 200. As described above, the releasable mechanism holding the rod 200 and rod holder 120 together disconnects when the two components are separated with sufficient force.

Figure 19:
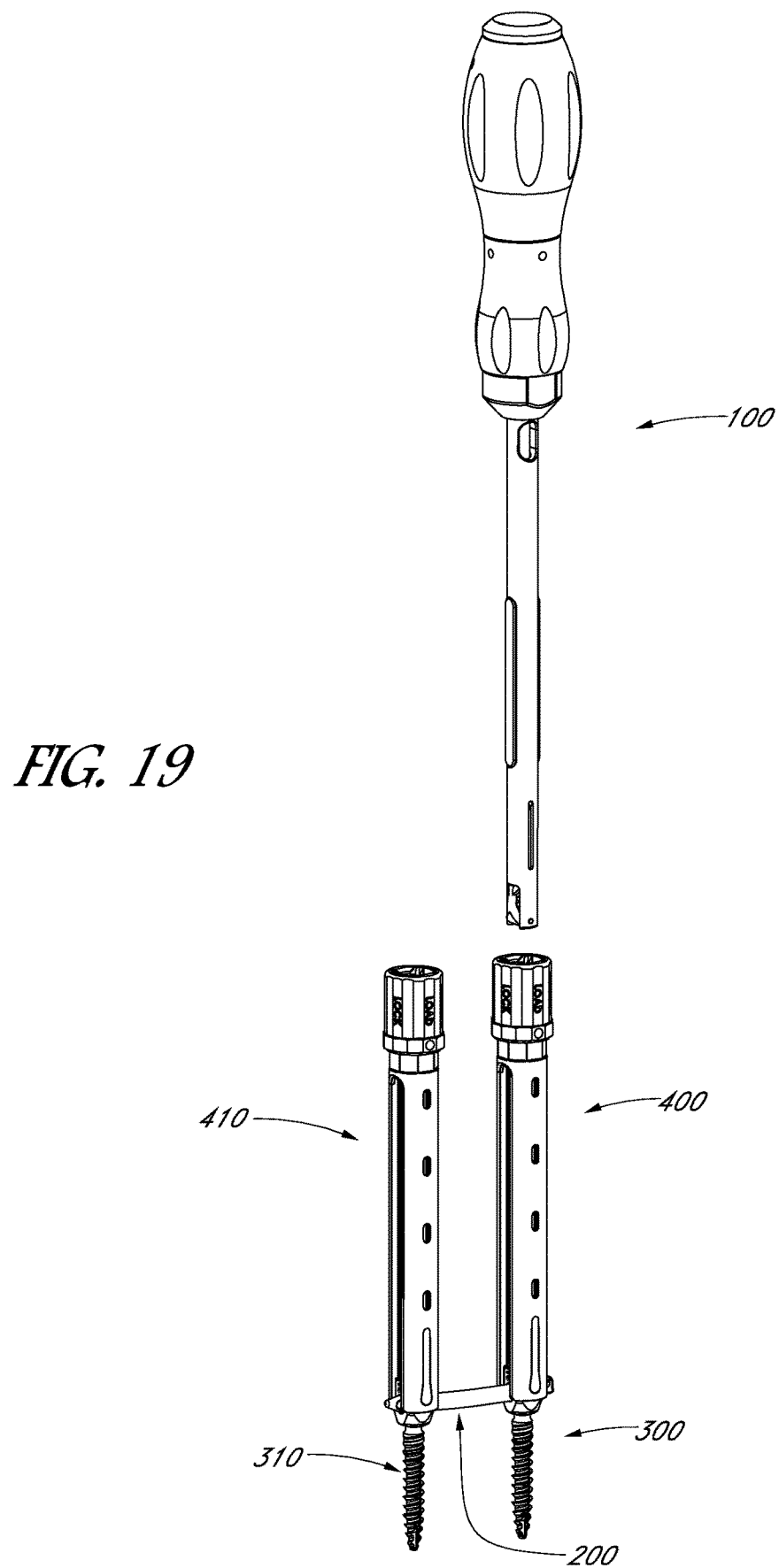
FIG. 19 is a perspective view of the rod inserter of FIG. 1 removed from a tower.

Once the rod holder 120 is fully retracted, the rod inserter 100 can be removed from the first tower 400, as illustrated in FIG. 19. In some embodiments, the fastener driver 500 can be inserted into the first tower 400 to attach a fastener to the first pedicle screw to secure the trailing end 202 of the rod 200. After the rod 200 is secured, the towers 400 and 410 can be removed and the one or more incisions closed.

In some configurations, a second set of anchoring devices is attached to the same vertebrae on the other side of the posterior arch. In other configurations, the second set of anchoring devices can be attached to different vertebrae. A second elongate member or rod 200 can be used to couple the second set of anchoring devices. In some configurations, the two rods 200 are generally parallel to each other. In other configurations, the two rods 200 can be at an angle to each other and/or different distances along the posterior-anterior direction.

Figure 20:
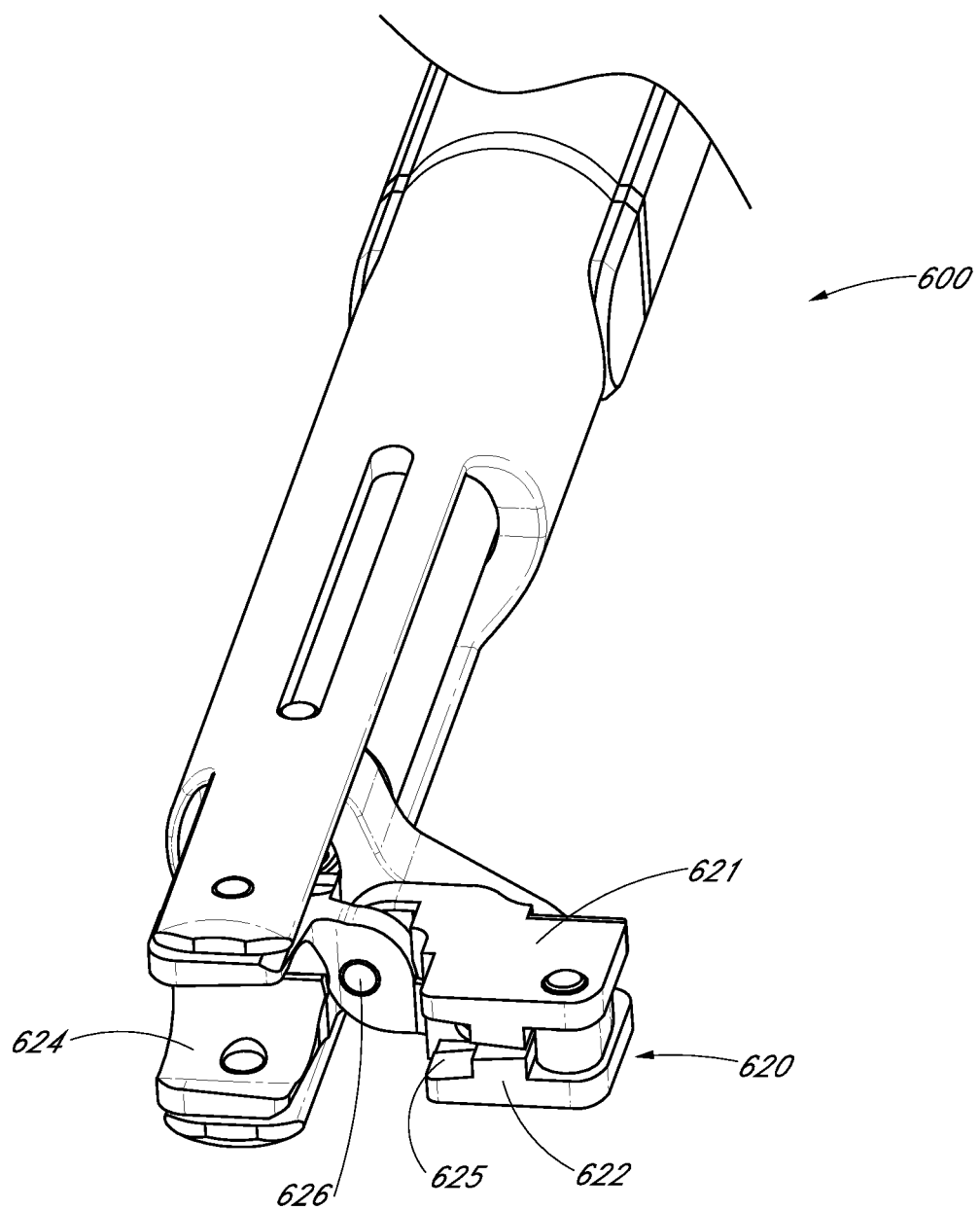
FIG. 20 is a close-up perspective view of a rod holder of a rod inserter, according to another embodiment of the present disclosure.

Another embodiment of a rod inserter 600 is illustrated in FIG. 20 with another embodiment of a rod holder 620. The rod holder 620 can have a mechanism 660 that is actuated to transition the rod holder 620 from a first configuration to a second configuration. In the first configuration, the rod holder 620 can grasp the rod and in the second configuration the rod holder can release the rod. In some embodiments, the mechanism 660 is a screw that is disposed between a first arm 621 and a second arm 622 and is configured to bring the arms 622, 622 toward each other, as described further below. In some embodiments, the mechanism can have a cam connection, angled surfaces, or other configuration to bring the arms together. The handle, tube 630 and linkage 650 can be similar to other embodiments of the rod inserter described above.

Figure 21:
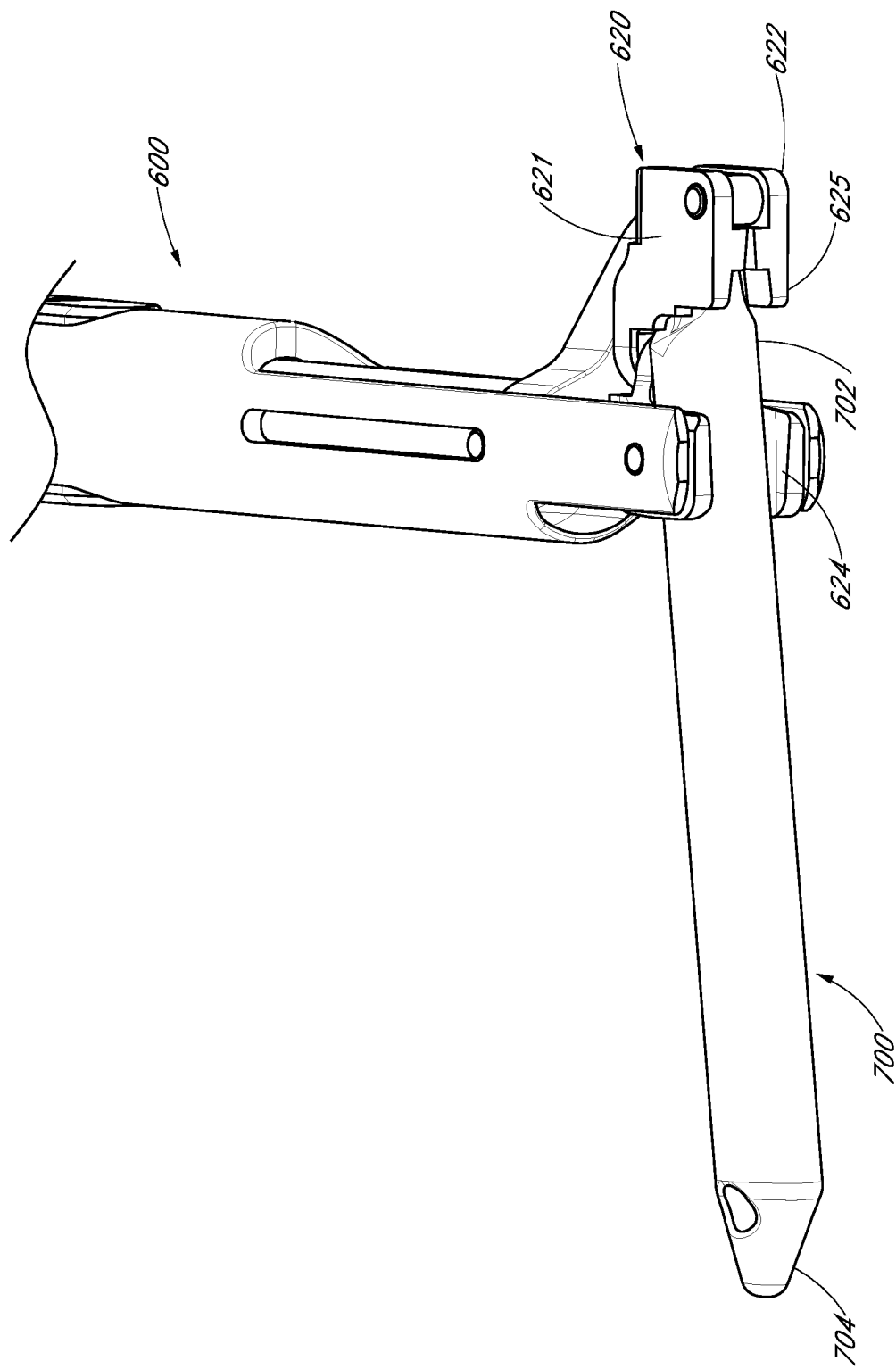
FIG. 21 is a close-up perspective view of the rod holder of FIG. 20, shown with a rod.
Figure 24:
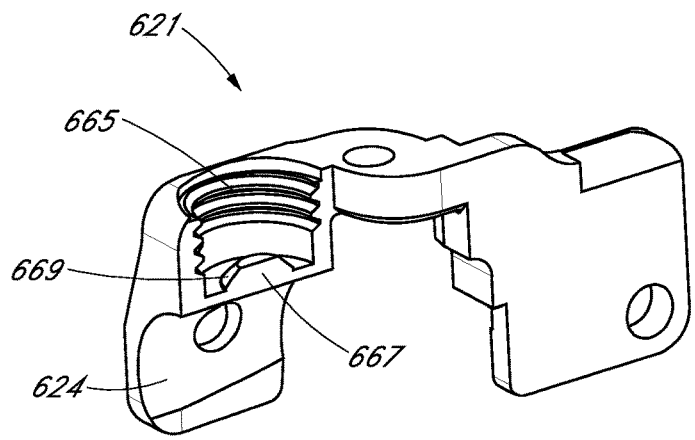
FIG. 24 is a perspective view of the first arm of the rod holder of FIG. 20.
Figure 25:
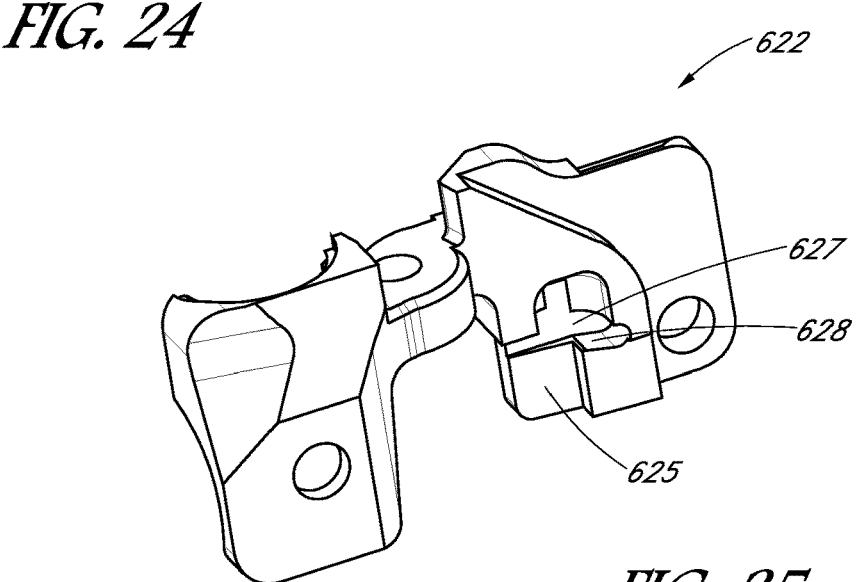
FIG. 25 is a perspective view of the second arm of the rod holder of FIG. 20.

With reference to FIGS. 20 and 21, the first arm 621 and second arm 622 can be configured to overlap each other and can be pivotally linked toward the center such that the arms 621, 622 move in a scissor-like motion. In the illustrated embodiment, the arms 621, 622 are connected by a hinge having a pin 626 with a longitudinal axis parallel with the axis of rotation of the arms 621, 622. In other embodiments, the arms can have any functional joint that provides pivotal movement, such as for example a ball-and-socket. As illustrated in FIGS. 20, 24 and 25, the arms 621, 622 can have a leading engagement portion 624 and a trailing engagement portion 625 that are configured to couple with a rod. The leading engagement portion 624 is comprised of side walls configured to extend around the rod 700. The inner surface of the leading engagement portion 624 can be curved to correspond to the curvature of the rod to help engage and secure the rod. The trailing engagement portion 625 is comprised of side walls with an opening between the walls configured to engage the trailing end 702 of the rod 700.

Figure 22:
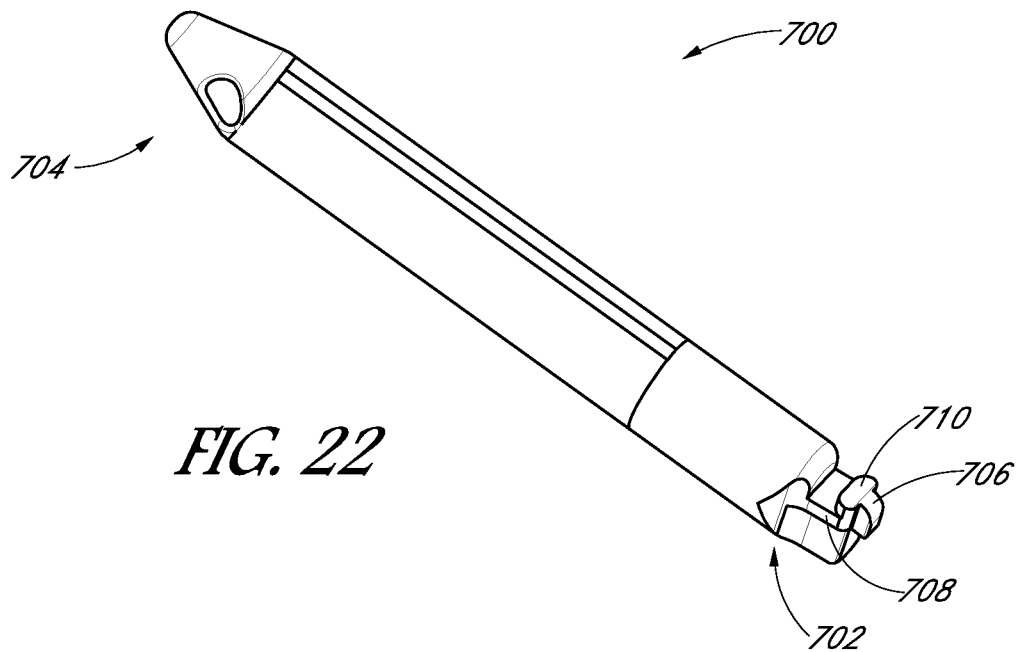
FIG. 22 is a perspective view of the rod of FIG. 21.
Figure 23:
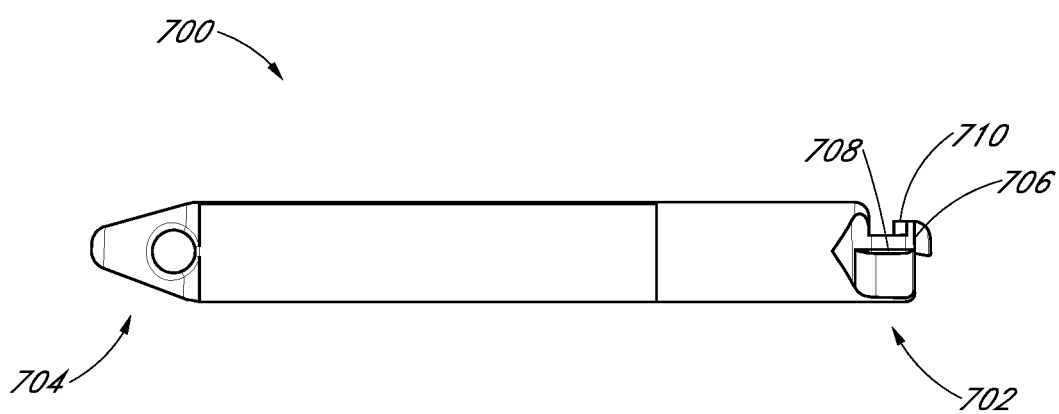
FIG. 23 is a side view of the rod of FIG. 21.

With reference to FIGS. 22 and 23, the rod 700 is an elongate member configured to extend between two or more bone anchors that are fixed to two or more vertebrae. In the illustrated embodiment, the rod 700 has an elongate cylindrical shape with a trailing end 702 and a leading end 704. In other embodiments, the rod can have other shapes, such as elongate members with an oval, square, rectangular, or polygonal cross-sectional shape. In some embodiments, the rod can be substantially straight or have a curve, which may help the fixation system to conform with the natural shape of the spinal anatomy.

In the illustrated embodiment, the trailing end 702 has a reduced thickness that fits between the side walls of the trailing engagement portion 625 of the rod holder 620. The trailing end 702 can have a knob 706 that couples with a cavity 627 in the trailing engagement portion 625 to help retain the rod 700 on the rod holder 620. In the illustrated embodiment, the knob 706 has flanges 708 that are configured to engage with shoulders 628 (see FIG. 25) in the cavity 627 of the trailing engagement portion 625 to help prevent the rod from falling out of the trailing engagement portion 625. The knob 706 can also have a projection 710 that blocks the rod 700 from moving longitudinally when coupled to the cavity 627 of the trailing engagement portion 625. In other embodiments, the knob can have other features to help secure the rod to a complementary cavity in the trailing engagement portion, such as for example hooks, magnets, textured surfaces, and the like.

Actuating the mechanism 660 can close the arms 621, 622 to a first configuration wherein the arms 621, 622 clamp around the rod 700. With reference to FIG. 21, the leading engagement portion 624 clamps onto the middle portion of rod 700 and the trailing engagement portion 625 clamps onto the trailing end 702 of the rod 700. In the embodiment illustrated in FIG. 24, the first arm 621 and the second arm 622 have a hole with internal threads 665. A dome 667 with sloped sides 669 can be disposed at the bottom of the hole and can be configured to engage the mechanism 660.

Figure 26:
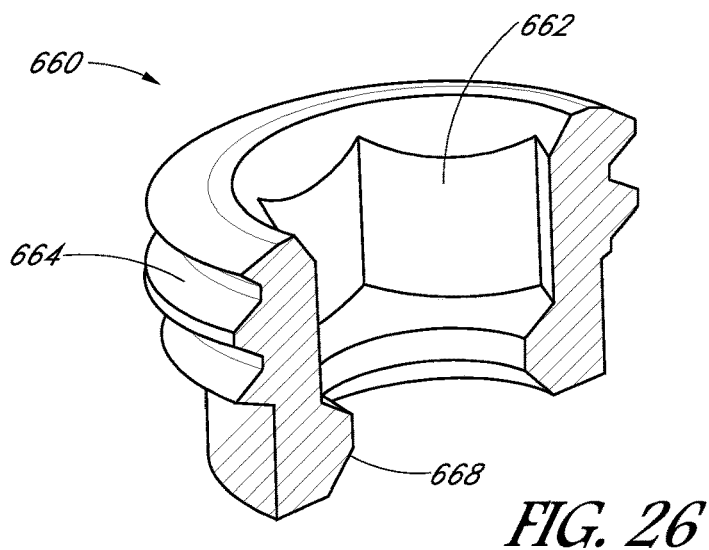
FIG. 26 is a perspective cross-sectional view of a mechanism of the rod holder of FIG. 20.

With reference to FIG. 26, the mechanism 660 can be a setscrew having a drive feature 662 on top and an aperture on the bottom with an angled bottom surface 668. The drive feature 662 is illustrated as a hex drive, but can be any of a plurality of different types of drive features, such as a Torx drive, slotted drive, and the like. The sides of the mechanism 660 can have external threads 664 that are complementary to the internal threads 665 of the arms 621, 622. When the mechanism 660 is screwed into the arms 621, 622, the angled bottom surface 668 of the mechanism 660 contacts the angled sides 669 of the dome 667. As the mechanism 660 is advanced further, the angled surfaces cooperate to squeeze the first arm 621 and second arm 622 together and close the leading engagement portion 624 in the first configuration. At the same time, the hinging action of the two arms 621, 622 closes the trailing engagement portion 625 in the first configuration.

The mechanism can be any of a plurality of different types of engagement devices configured to draw the two arms together, such as for example a clamp, a cam mechanism, or a fastener. In some embodiments, the arms can clamp in other ways. For example, the rod holder may pivot along its longitudinal axis and a wedge inserted in the top portion of the rod holder can close the engagement portions on the bottom portion of the rod holder. In another example, advancing a mechanism can drive a wedge between the rod holder and the rod to secure the rod. Other arrangements for securing the rod are also contemplated.

Figure 27:
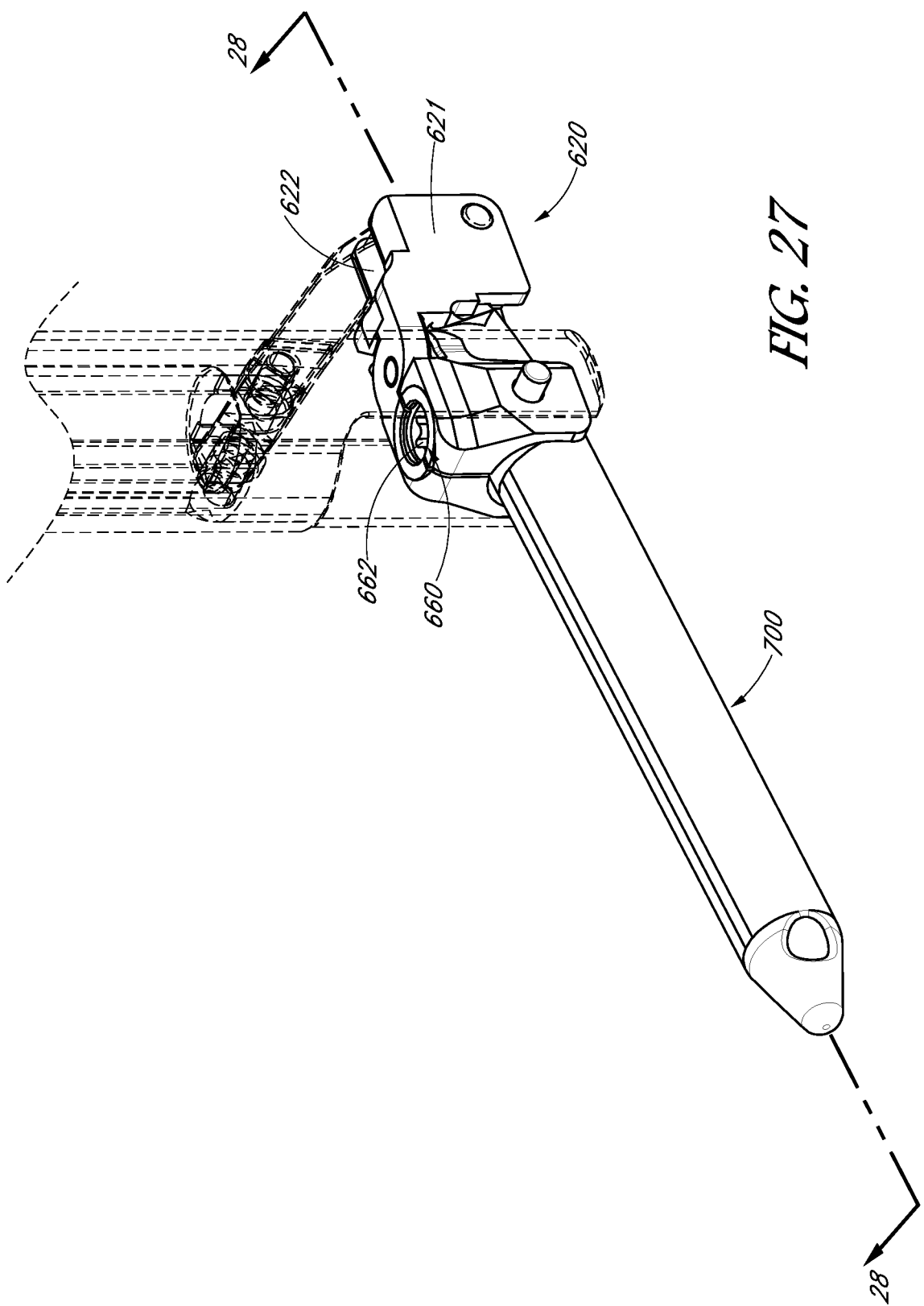
FIG. 27 is a close-up perspective view of the rod holder of FIG. 20, shown with a rod and portions of the rod inserter as transparent.
Figure 28:
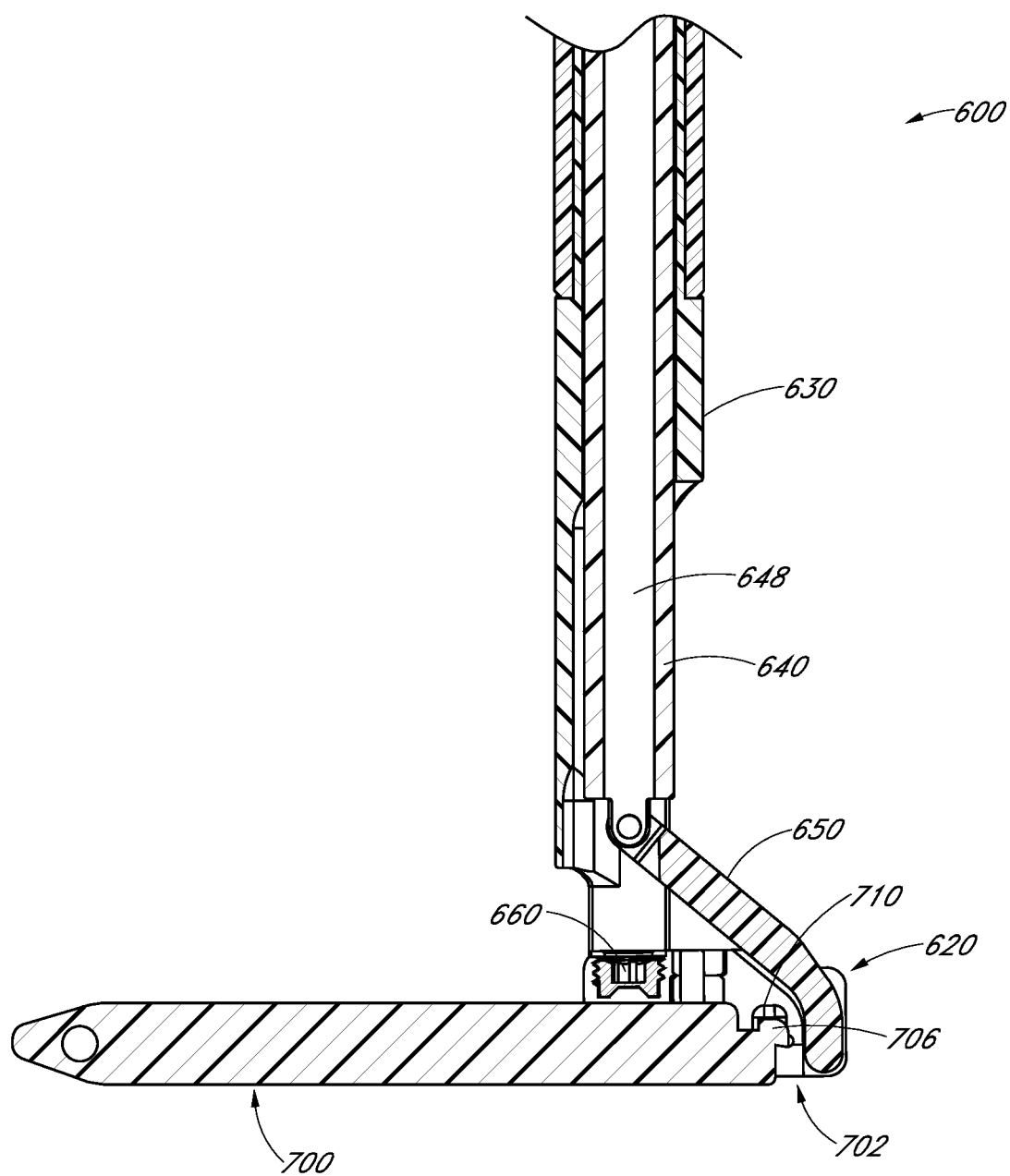
FIG. 28 is a close-up cross-sectional side view of the rod holder of FIG. 27.

With reference to FIGS. 27 and 28, when the rod holder is generally perpendicular to the longitudinal axis of the shaft 640, the drive feature 662 of the mechanism 660 is generally aligned with the longitudinal axis of the shaft 640.

As illustrated in FIG. 28, the shaft 640 can have a channel 648 that extends through the longitudinal length of the shaft 640. The channel 648 is configured to provide access to the mechanism 660 from the top of the rod inserter 600. A drive tool can be inserted through the channel 648 to engage the mechanism 660 and change the rod holder 620 between the first and second configurations. When the rod holder is generally parallel to the longitudinal axis of the shaft 640, the mechanism 660 can be accessed and actuated through a cutout 638 on the side of the tube 630, as illustrated in FIGS. 27 and 28.

Figure 29:
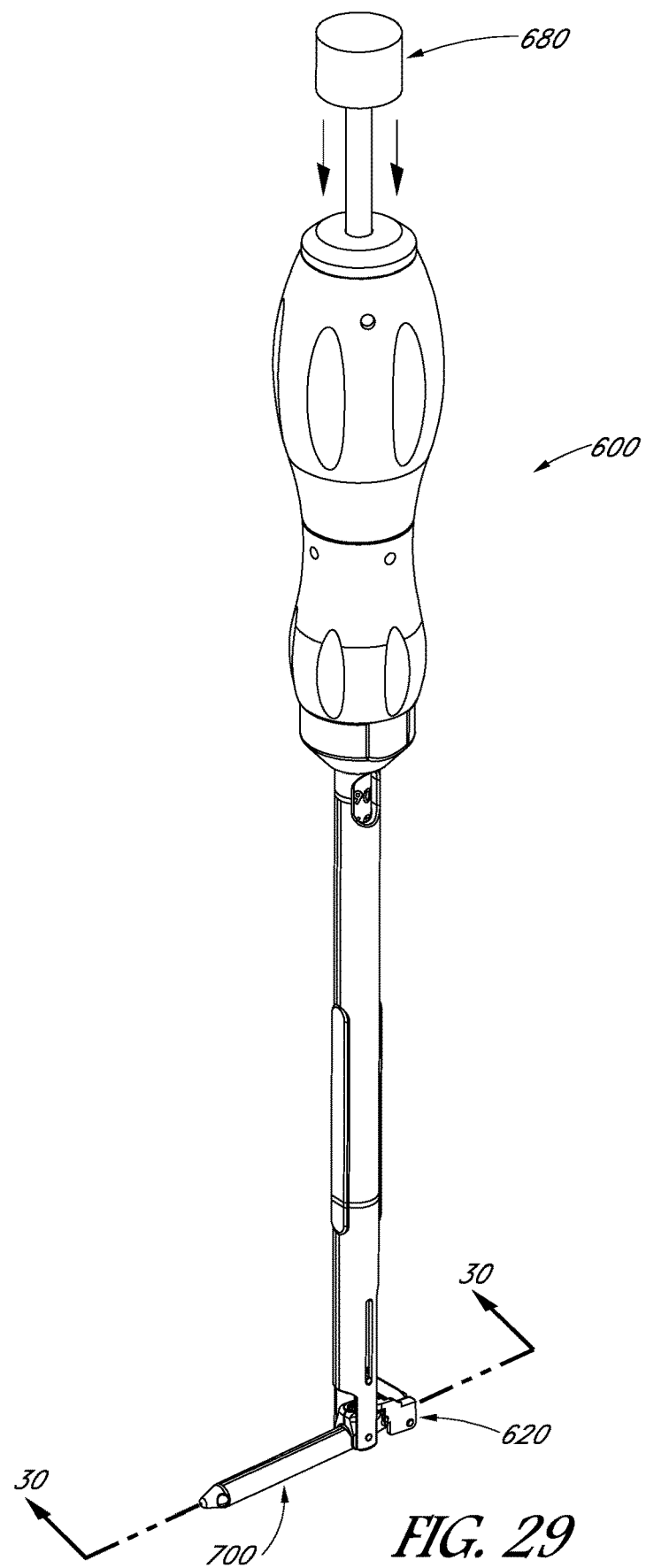
FIG. 29 is a perspective view of the rod inserter of FIG. 20, shown with a drive tool and a rod.
Figure 30:
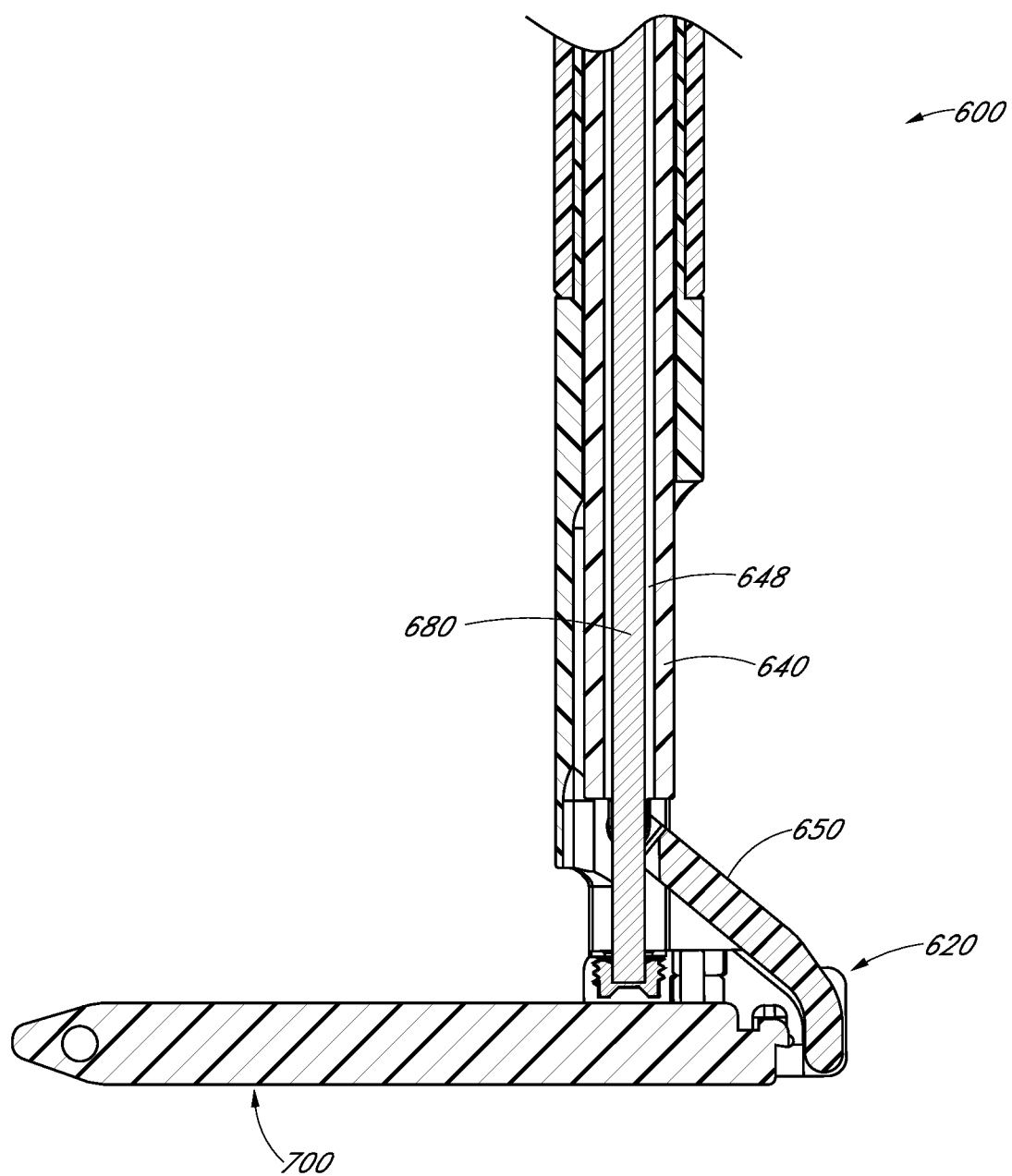
FIG. 30 is a close-up cross-sectional side view of the rod holder of FIG. 29, with the drive tool and rod.

FIG. 29 illustrates an embodiment of a rod inserter 600 with a drive tool 680 inserted through the rod inserter 600 to actuate the mechanism 660. The drive tool 680 protrudes proximally from the handle of the rod inserter 600 and can be conveniently manipulated from outside of the surgical incision. As illustrated in FIG. 30, the drive tool 680 extends through the channel 648 of the shaft 640 and the distal end of the drive tool 680 is configured to engage the drive feature 662 of the mechanism 660. As discussed above, the drive feature 662 can be a hex drive, a Torx drive, slotted, or any other functional drive feature. The distal end of the drive tool 680 has a complementarily shaped hex head, Torx head, flathead, etc. to engage the drive feature 662.

Methods of using the alternative embodiments of the rod inserter are similar to as described above for other embodiments. The vertebral column is accessed and one or more vertebrae are identified and accessed. In a minimally invasive technique, the vertebrae can be accessed through two small incisions that are made near the selected vertebrae. The incisions can be just large enough to accommodate access cannulas or towers. In some embodiments, the vertebral column can be accessed through a single incision that is large enough to access the two or more vertebrae in an open procedure.

As described above, a first pedicle screw and a first tower can be attached to a first vertebra. A second pedicle screw and a second tower can be attached to a second vertebra. Then, the rod inserter 600 with the rod 700 attached can be positioned above one of the towers. The rod 700 is generally longitudinally aligned with the rod inserter 600 in preparation for insertion in the first tower. The rod inserter 600 is oriented such that the rod 700 can be angled toward the second tower.

The rod inserter 600 can have alignment features that engage with features on the towers to help orient the rod inserter 600 in the desired direction, as described above in other embodiments. In the illustrated embodiments, the alignment feature couples with slots in the tower, which help orient the rod inserter 600 in the proper direction for advancing the rod 700 toward the second tower. The alignment feature can also help prevent the rod 700 from being inadvertently misaligned or rotated about the longitudinal axis of the tower.

As the rod 700 approaches or reaches the top of the first pedicle screw, the actuator portion of the handle can be activated (e.g., rotated) to start angling the rod 700 relative to the longitudinal axis of the first tower and rod inserter 600. The leading end 704 of the rod 700 can move out of the tower through openings that are disposed on the sides of the towers. As the actuator portion is further activated, the leading end 704 of the rod 700 continued to move toward the second tower. The rod inserter 600 can be moved further distally down the first tower as the rod 700 is angled. The leading end 704 of the rod 700 can move through side openings in the second tower and through the channel of the second tower.

The rod 700 can be seated in the heads of the pedicle screws, where the rod 700 can be generally perpendicular to the tube of the rod inserter 600, or generally parallel with the spinal column. In other embodiments, the rod 700 can be at other angles to suit the positions of the pedicle screws and/or anatomy of the patient. In some embodiments, a fastener driver is inserted in the second tower to deliver and couple a fastener, such as a threaded cap, to the head of a pedicle screw. The fastener is tightened against the rod 700 to fix the leading end 704 of the rod 700.

A drive tool 680 can be inserted through the channel 648 of the rod inserter 600 from the proximal end to the rod holder 620 at the distal end. The drive tool 680 is configured to engage and actuate the mechanism 660. As described above, actuating the mechanism 660 releases the rod 700 from the rod holder 620. After the rod 700 is released from the rod holder 620, the drive tool 680 can be removed from the rod inserter 600.

The actuator portion can be activated in reverse to retract the rod holder 620 back into the tube. Once the rod holder 620 is retracted, the rod inserter 600 can be removed from the first tower. In some embodiments, a fastener driver can be inserted into the first tower to attach a fastener to the first pedicle screw to secure the trailing end 702 of the rod 700. After the rod 700 is secured, the towers can be removed and the one or more incisions closed.

In some configurations, a second set of anchoring devices is attached to the same vertebrae on the other side of the posterior arch. In other configurations, the second set of anchoring devices can be attached to different vertebrae. A second elongate member or rod 700 can be used to couple the second set of anchoring devices. In some configurations, the two rods 700 are generally parallel to each other. In other configurations, the two rods 700 are at an angle to each other.

Although certain embodiments, features, and examples have been described herein, it will be understood by those skilled in the art that many aspects of the methods and devices illustrated and described in the present disclosure may be differently combined and/or modified to form still further embodiments. For example, any one component of the device illustrated and described above can be used alone or with other components without departing from the spirit of the present disclosure. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present disclosure. Thus, it is intended that the scope of the present disclosure should not be limited by the particular embodiments described above, but should be determined only by a fair reading of the claims that follow.

What is claimed is:

1. A method of delivering a rod onto a fixation system, the method comprising:
   providing a rod inserter comprising:
      a first member comprising an elongate tube with a passage extending from a proximal end to a distal end;
      a second member comprising an elongate shaft configured to move along the passage of the first member;
      a third member comprising a first end and a second end, the first end coupled to the second member at the distal end;
      a rod holder comprising a leading end coupled to the distal end of the first member and a trailing end coupled to the second end of the third member, the rod holder configured to rotate from an aligned configuration wherein a longitudinal axis of the rod holder is generally parallel with a longitudinal axis of the second member, to an angled configuration wherein the longitudinal axis of the rod holder is at an angle to the longitudinal axis of the second member, wherein the leading end is distal to the trailing end in the aligned configuration; and
      a rod releasably coupled to the rod holder, wherein the rod holder is configured to transition between a clamping configuration and a release configuration;
   inserting the rod longitudinally through an access channel of a first anchoring device; and
   activating an actuator on the rod inserter to transition the rod holder from the aligned configuration to the angled configuration; and
   transitioning the rod holder from the clamping configuration to the release configuration.

2. The method of delivering a rod of claim 1, wherein the rod holder automatically releases the rod when the rod holder is transitioned from the angled configuration toward the aligned configuration.

3. The method of delivering a rod of claim 1, further comprising securing the rod to the first anchoring device.

4. The method of delivering a rod of claim 3, wherein securing the rod to the first anchoring device comprises fastening a threaded cap onto the first anchoring device.

5. The method of delivering a rod of claim 1, wherein the first anchoring device comprises a pedicle screw with a head adapted to receive the rod.

6. The method of delivering a rod of claim 1, wherein the second member comprises a longitudinal channel for transitioning the rod holder from the clamping configuration to the release configuration from the proximal end.

7. The method of delivering a rod of claim 6, wherein a drive tool is used for transitioning the rod holder from the clamping configuration to the release configuration.

8. The method of delivering a rod of claim 1, wherein the third member comprises one or more linkages.

9. The method of delivering a rod of claim 1, wherein activating the actuator comprises rotating a handle.

10. The method of delivering a rod of claim 9, wherein the handle comprises threads that engage complementary threads on the second member to move the second member longitudinally.

11. The method of delivering a rod of claim 1, further comprising an indicator corresponding to the orientation of the rod holder relative to the second member.

12. The method of delivering a rod of claim 1, wherein the rod inserter further comprises protrusions on the first member that are insertable into longitudinal slots on an access tower.

* * * * *